US009314499B2

(12) United States Patent
Wang et al.

(10) Patent No.: US 9,314,499 B2
(45) Date of Patent: Apr. 19, 2016

(54) ANNEXIN A2 AND TISSUE PLASMINOGEN ACTIVATOR FOR TREATING VASCULAR DISEASE

(71) Applicant: The General Hospital Corporation, Boston, MA (US)

(72) Inventors: Xiaoying Wang, West Roxbury, MA (US); Eng Lo, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/197,988

(22) Filed: Mar. 5, 2014

(65) Prior Publication Data

US 2014/0227350 A1    Aug. 14, 2014

Related U.S. Application Data

(63) Continuation of application No. 12/918,726, filed as application No. PCT/US2009/001057 on Feb. 19, 2009, now abandoned.

(60) Provisional application No. 61/030,033, filed on Feb. 20, 2008.

(51) Int. Cl.
*A61K 38/17* (2006.01)
*A61K 38/49* (2006.01)
*A61K 38/00* (2006.01)

(52) U.S. Cl.
CPC ............. *A61K 38/17* (2013.01); *A61K 38/1709* (2013.01); *A61K 38/49* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 5,364,634 | A | 11/1994 | Lew | 424/451 |
| 6,962,903 | B2 | 11/2005 | Allison | 435/69.1 |
| 7,115,408 | B1 | 10/2006 | Rich | 424/94.1 |
| 7,250,271 | B2 | 7/2007 | Waisman et al. | 435/69.1 |
| 2002/0016625 | A1 | 2/2002 | Falotico et al. | 604/500 |
| 2002/0155160 | A1* | 10/2002 | Leach et al. | 424/493 |
| 2003/0216699 | A1 | 11/2003 | Falotico | 424/423 |

OTHER PUBLICATIONS

Ishii et al., Circ Res., 2001;89: 1240-1245.*
Kimata et al., Chem Pharm. Bull., 1991; 39: 3327-3330.*
Burggraf et al., Eur J Neurosci. 2004; 20: 2903-8.*
Roda et al., JBC, 2003; 278: 5702-5709.*
Aarli, et al., "Inhibition of Phytohaemagglutinin-Induced Lymphoproliferation by Soluble Annexin II in Sera from Patients with Renal Cell Carcinoma." *APMIS*, 105(9):699-704 (1997).
Angelillo-Scherrer, et al., "Deficiency or Inhibition of Gas6 Causes Platelet Dysfunction and Protects Mice against Thrombosis." *Nat Med*, 7(2):215-221 (2001).
Armstead, et al., Neutralizing the neurotoxic effects of exogenous and endogenous tPA. *Nat Neurosci*. 9(9):1150-1155 (2006).
Asahi, et al., "Reduction of Tissue Plasminogen Activator-Induced Hemorrhage and Brain Injury by Free Radical Spin Trapping after Embolic Focal Cerebral Ischemia in Rats." *J Cereb Blood Flow Metab*, 20(3):452-457 (2000).
Benchenane, et al., "Equivocal Roles of Tissue-Type Plasminogen Activator in Stroke-Induced Injury." *Trends Neurosci*, 27(3):155-160 (2004).
Benchenane, et al., "Tissue-Type Plasminogen Activator Crosses the Intact Blood-Brain Barrier by Low-Density Lipoprotein Receptor-Related Protein-Mediated Transcytosis." *Circulation*, 111(17):2241-2249 (2005).
Benz and Hofmann, "Annexins: From Structure to Function." *Biol Chem*, 378(3-4):177-183 (1997).
Brott, et al., "Urgent Therapy for Stroke. Part I. Pilot Study of Tissue Plasminogen Activator Administered within 90 Minutes." *Stroke*, 23(5):632-640 (1992).
Cheng, et al., "Activated Protein C Inhibits Tissue Plasminogen Activator-Induced Brain Hemorrhage." *Nat Med*, 12(11):1278-1285 (2006).
Chow, et al., "Thrombin Receptor Activating Peptide (SFLLRN) Potentiates Shear-Induced Platelet Microvesiculation." *J Lab Clin Med*, 135(1):66-72 (2000).
Ding, et al., "Analysis of Combined Treatment of Embolic Stroke in Rat with R-Tpa and a GPIIB/IIIA Inhibitor." *J Cereb Blood Flow Metab*, 25(1):87-97 (2005).
Falk, et al., "Interrelationship between Atherosclerosis and Thrombosis." In *Cardiovascular Thrombosis: Thrombocardiology and Thromboneurology* (Vanstraete, Ed.), pp. 45-58, Lipincott-Raven Publishers, Philadelphia (1998).
Grotta, et al., "Intravenous Tissue-Type Plasminogen Activator Therapy for Ischemic Stroke: Houston Experience 1996 to 2000." *Arch Neurol*, 58(12):2009-2013 (2001).
Hajjar, et al., "An Endothelial Cell Receptor for Plasminogen/Tissue Plasminogen Activator. I. Identity with Annexin II." *J Biol Chem*, 269(33):21191-21197 (1994).
Hajjar and Menell, "Annexin II: A Novel Mediator of Cell Surface Plasmin Generation." *Ann N Y Acad Sci*, 811:337-349 (1997).
Hajjar and Krishnan, "Annexin II: A Mediator of the Plasmin/Plasminogen Activator System." *Trends Cardiovasc Med*, 9(5):128-138 (1999).
Hajjar and Acharya, "Annexin II and Regulation of Cell Surface Fibrinolysis." *Ann N Y Acad Sci*, 902:265-271 (2000).
Haley, et al., "Urgent Therapy for Stroke. Part II. Pilot Study of Tissue Plasminogen Activator Administered 91-180 Minutes from Onset." *Stroke*, 23(5):641-645 (1992).

(Continued)

*Primary Examiner* — Christina Borgeest
(74) *Attorney, Agent, or Firm* — Medlen & Carroll, LLP

(57) ABSTRACT

The use of tPA to treat hemorrhagic transformation, neurotoxicity has been limited to short treatment time windows because a high dose of tPA required to generate sufficient amounts of the enzyme plasmin for clot lysis. The present invention combines tPA with recombinant Annexin A2 resulting in thrombolysis without hemorrhagic transformation at delayed times after stroke. This embodiment allows the administration of a lower, non-neurotoxic, tPA dose. Our results suggest this novel combination for stroke therapy may greatly improve both efficacy and safety, and prolong tPA therapeutic time window.

20 Claims, 6 Drawing Sheets

(56) References Cited

OTHER PUBLICATIONS

Harada, et al., "Tissue Plasminogen Activator Extravasated through the Cerebral Vessels: Evaluation Using a Rat Thromboembolic Stroke Model." *Thromb Haemost*, 94(4):791-796 (2005).
Hollopeter, et al., "Identification of the Platelet Adp Receptor Targeted by Antithrombotic Drugs." *Nature*, 409(6817):202-207 (2001).
Ishimoto and Nakano, "Release of a Product of Growth Arrest-Specific Gene 6 from Rat Platelets." *FEBS Lett*, 466(1):197-199 (2000).
Jeremias, et al., "Stent Thrombosis after Successful Sirolimus-Eluting Stent Implantation." *Circulation*, 109(16):1930-1932 (2004).
Kaur, et al., "The Neurotoxicity of Tissue Plasminogen Activator?" *J Cereb Blood Flow Metab*, 24(9):945-963 (2004).
Kim and Hajjar, "Annexin II: A Plasminogen-Plasminogen Activator Co-Receptor." *Front Biosci*, 7:d341-348 (2002).
Knecht, et al., "Evaluation of Plasma D-Dimer in the Diagnosis and in the Course of Fibrinolytic Therapy of Deep Vein Thrombosis and Pulmonary Embolism." *Thromb Res*, 67(2):213-220 (1992).
Korninger and Collen,"Studies on the Specific Fibrinolytic Effect of Human Extrinsic (Tissue-Type) Plasminogen Activator in Human Blood and in Various Animal Species in Vitro." *Thromb Haemost*, 46(2):561-565 (1981).
Lapchak, et al., "Metalloproteinase Inhibition Reduces Thrombolytic (Tissue Plasminogen Activator)-Induced Hemorrhage after Thromboembolic Stroke." *Stroke*, 31(12):3034-3040 (2000).
Lapchak, et al., "Microplasmin: A Novel Thrombolytic That Improves Behavioral Outcome after Embolic Strokes in Rabbits." *Stroke*, 33(9):2279-2284 (2002a).
Lapchak, et al., "Coadministration of Nxy-059 and Tenecteplase Six Hours Following Embolic Strokes in Rabbits Improves Clinical Rating Scores." *Exp Neurol*, 188(2):279-285 (2004).
Levine, et al., "Hemorrhagic Complications of Anticoagulant Treatment." *Chest*, 119(1 Suppl):108S-121S (2001).
Marler and Goldstein, "Medicine. Stroke—tPA and the Clinic." *Science*, 301(5640):1677 (2003).
Mehta, et al., "Risk of Intracranial Haemorrhage with Bolus Versus Infusion Thrombolytic Therapy: A Meta-Analysis." *Lancet*, 356(9228):449-454 (2000).
Merten, et al., "Platelet Microparticles Promote Platelet Interaction with Subendothelial Matrix in a Glycoprotein Iib/Iiia-Dependent Mechanism." *Circulation*, 99(19):2577-2582 (1999).
Miller, et al., "Degradation Rates of Oral Resorbable Implants (Polylactates and Polyglycolates): Rate Modification with Changes in Pla/Pga Copolymer Ratios." *J Biomed Mater Res*, 11(5):711-719 (1977).
Morris, et al., "Extension of the Therapeutic Window for Recombinant Tissue Plasminogen Activator with Argatroban in a Rat Model of Embolic Stroke." *Stroke*, 32(11):2635-2640 (2001).
Nassar, et al., "In Vitro and in Vivo Effects of Tpa and Pai-1 on Blood Vessel Tone." *Blood*, 103(3):897-902 (2004).
Nicole, et al., "The Proteolytic Activity of Tissue-Plasminogen Activator Enhances Nmda Receptor-Mediated Signaling." *Nat Med*, 7(1):59-64 (2001).
Novokhatny, et al., "Tissue-Type Plasminogen Activator (Tpa) Interacts with Urokinase-Type Plasminogen Activator (UPA) Via Tpa's Lysine Binding Site. An Explanation of the Poor Fibrin Affinity of Recombinant Tpa/Upa Chimeric Molecules." *J Biol Chem*, 270(15):8680-8685 (1995).
Pfefferkorn and Rosenberg, "Closure of the Blood-Brain Barrier by Matrix Metalloproteinase Inhibition Reduces Rtpa-Mediated Mortality in Cerebral Ischemia with Delayed Reperfusion." *Stroke*, 34(8):2025-2030 (2003).
Putney and Burke, "Improving Protein Therapeutics with Sustained-Release Formulations." *Nat Biotechnol*, 16(2):153-157 (1998).
Rawles, "Quantification of the Benefit of Earlier Thrombolytic Therapy: Five-Year Results of the Grampian Region Early Anistreplase Trial (Great)." *J Am Coll Cardiol*, 30(5):1181-1186 (1997).
Ribo, et al., "Acute Hyperglycemia State Is Associated with Lower tPA-Induced Recanalization Rates in Stroke Patients." *Stroke*, 36(8):1705-1709 (2005).
Rouhiainen, et al., "Occurrence of Amphoterin (Hmg1) as an Endogenous Protein of Human Platelets That Is Exported to the Cell Surface Upon Platelet Activation." *Thromb Haemost*, 84(6):1087-1094 (2000).
Sakharov and Rijken, "Superficial Accumulation of Plasminogen During Plasma Clot Lysis." *Circulation*, 92(7):1883-1890 (1995).
Santilli, "Fibrin Sheaths and Central Venous Catheter Occlusions: Diagnosis and Management." *Tech Vasc Interv Radiol*, 5(2):89-94 (2002).
Schwartz and Reidy, "Common Mechanisms of Proliferation of Smooth Muscle in Atherosclerosis and Hypertension." *Hum Pathol*, 18(3):240-247 (1987).
Sena, et al., "How Can We Improve the Pre-Clinical Development of Drugs for Stroke?" *Trends Neurosci*, 30(9):433-439 (2007).
Siever and Erickson, "Extracellular Annexin Ii." *Int J Biochem Cell Biol*, 29(11):1219-1223 (1997).
Strbian, et al., "Mast Cell Stabilization Reduces Hemorrhage Formation and Mortality after Administration of Thrombolytics in Experimental Ischemic Stroke." *Circulation*, 116(4):411-418 (2007).
Sun, et al., "Interaction of Annexin V and Platelets: Effects on Platelet Function and Protein S Binding." *Thromb Res*, 69(3):289-296 (1993).
Tanaka, et al., "Efficacy of Recombinant Annexin 2 for Fibrinolytic Therapy in a Rat Embolic Stroke Model: A Magnetic Resonance Imaging Study." *Brain Res*, 1165:135-143 (2007).
Tsirka, et al., "Neuronal Cell Death and tPA." *Nature*, 384(6605):123-124 (1996).
Tsirka, "Clinical Implications of the Involvement of tPA in Neuronal Cell Death." *J Mol Med (Berl)*, 75(5):341-347 (1997).
Walles, et al., "Functional Neointima Characterization of Vascular Prostheses in Human." *Ann Thorac Surg*, 77(3):864-868 (2004).
Wang, et al., "Lipoprotein Receptor-Mediated Induction of Matrix Metalloproteinase by Tissue Plasminogen Activator." *Nat Med*, 9(10):1313-1317 (2003).
Wang, et al., "Mechanisms of Hemorrhagic Transformation after Tissue Plasminogen Activator Reperfusion Therapy for Ischemic Stroke." *Stroke*, 35(11 Suppl 1):2726-2730 (2004).
Zhang, et al., "Adjuvant Treatment with Neuroserpin Increases the Therapeutic Window for Tissue-Type Plasminogen Activator Administration in a Rat Model of Embolic Stroke." *Circulation*, 106(6):740-745 (2002).
Zhang, et al., "Treatment of Embolic Stroke in Rats with Bortezomib and Recombinant Human Tissue Plasminogen Activator." *Thromb Haemost*, 95(1):166-173 (2006).
Zivin, "Thrombolytic Stroke Therapy: Past, Present, and Future." *Neurology*, 53(1):14-19 (1999).
Cesarman-Maus, et al., "Autoantibodies against the Fibrinolytic Receptor, Annexin 2, in Antiphospholipid Syndrome." *Blood*, 107(11):4375-4382 (2006).
Grupper, et al., "Ischemic Stroke, Aortic Dissection, and Thrombolytic Therapy—the Importance of Basic Clinical Skills " *J Gen Intern Med*, 22(9):1370-1372 (2007).
Lansberg, et al., "Risk Factors of Symptomatic Intracerebral Hemorrhage after tPA Therapy for Acute Stroke." *Stroke*, 38(8):2275-2278 (2007).
Burggraf, et al., "Rt-Pa Causes a Significant Increase in Endogenous U-Pa During Experimental Focal Cerebral Ischemia." *Eur J Neurosci*, 20(11):2903-2908 (2004).
Clark, et al., "Recombinant Tissue-Type Plasminogen Activator (Alteplase) for Ischemic Stroke 3 to 5 Hours after Symptom Onset. The Atlantis Study: A Randomized Controlled Trial. Alteplase Thrombolysis for Acute Noninterventional Therapy in Ischemic Stroke." *Jama*, 282(21):2019-2026 (1999).
Kimata, et al., "Fibrinolytic Effect of Tissue Plasminogen Activator on Cerebral Embolism in Stroke-Prone Spontaneously Hypertensive Rats." *Chem Pharm Bull (Tokyo)*, 39(12):3327-3330 (1991).
Roda, et al., "New Insights into the Tpa-Annexin A2 Interaction. Is Annexin A2 Cys8 the Sole Requirement for This Association?". *J Biol Chem*, 278(8):5702-5709 (2003).
Fan, et al., "Annexin A2: A Tissue Plasminogen Activator Amplifier for Thrombolytic Stroke Therapy." Stroke. 41:S54-S58 (2010).
Zhu, et al., "Annexin A2 combined with low-dose tPA improves thrombolytic therapy in a rat model of focal embolic stroke." Journal of Cerebral Blood Flow & Metabolism, 1-10 (2010).

\* cited by examiner

SEQ ID NO: 1 a.

MEQHFLGCVKRAWDSAEVAPEPQPPPIVSSEDRGPWPLPLYP
VLGEYSLDSCDLGLLSSPCWRLPGVYWQNGLSPGVQSTLEPS
TAKPTEFSWPGTQKQQEAPVEEVGQAEEPDRLRLQQLPWSS
PLHPWDRQQDTEVCDSGCLLERRHPPALQPWRHLPGFSDCL
EWILRVGFAAFSVLWACCSRICGAKQP b. SEQ ID NO: 2

```
1    gacccacgcg tccggttcta tgtactctct aaaatgttat cgttttcatt tgtctactaa
61   ttttcgagca tttgttacta ctgagtttct taatatctga ctggcctccg cccacgggct
121  ctgcagagca taaatactca ggctgatggt agtgcagaga ctctccctcc ttgatcagcg
181  caaacgttgg tctgaggctt gagggatgga gcaacatttt cttggctgtg tgaagcgggc
241  ttgggattcc gcagaggtgg cgccagagcc ccagcctcca cctattgtga gttcagaaga
301  tcgtgggccg tggcctcttc ctttgtatcc agtactagga gagtactcac tggacagctg
361  tgatttggga ctgctttcca gcccttgctg gcggctgccc ggagtctact ggcaaaacgg
421  actctctcct ggagtccaga gcaccttgga accaagtaca gcgaagccca ctgagttcag
481  ttggccgggg acacagaagc agcaagaggc acccgtagaa gaggtggggc aggcagagga
541  acccgacaga ctcaggctcc agcagcttcc ctggagcagt cctctccatc cctgggacag
601  acagcaggac accgaggtct gtgacagcgg gtgccttttg gaacgccgcc atcctcctgc
661  cctccagccg tggcgccacc tcccgggttt ctcagactgc ctggagtgga ttcttcgcgt
721  tggttttgcc gcgttctctg tactctgggc gtgctgttca cggatctgtg gagctaagca
781  gccttagata gcagcagaag gcttttggga ttctcctcct tgaaaagatt ctcagttacc
841  aaacgtctcc acctagaaaa taaaaataca ttaagatgtg ctttcattgc tggttgtcag
901  tttttaaatt ctcttttcc cttatgtttc tttcttgttt cgcgtcgctt attactttca
961  gtttccttgt attttaaata ttggtatttc attaaatatt tcattcgtat ctgttttcac
1021 tttgagaaat ctattttacg attgtagaat tcttagagtt tttggcaaat ttaaaatttg
1081 ttttttccca ttgtatttta aaatcttatt cctactattt ttctaattat tgcttttttaa
1141 atgtattgtt tgtttacatt taattttaaa aaaaaaaaa aa
```

ANNEXIN A2 AND TISSUE PLASMINOGEN ACTIVATOR FOR TREATING VASCULAR DISEASE

A Sequence Listing has been submitted in an ASCII text file named 16910_ST25.txt, created on Jul. 29, 2013, consisting of 4 KB, the entire content of which is herein incorporated by reference.

FIELD OF INVENTION

The present invention is related to the field of vascular disorders. In particular, the present invention is related to the treatment and management of diseases including, but not limited to, stroke, myocardial infarction, deep vein thrombosis, or pulmonary embolism. For example, a patient having suffered a vascular disorder may be administered a composition comprising tPA and Annexin A2. In such cases, the tPA dose may be reduced such that the risk of hemorrhagic side effects are minimal.

BACKGROUND

Each year, about 600,000 American suffer from stroke. Thrombolytic therapy with tissue plasminogen activator (tPA) is the only FDA-approved medicine for achieving both vascular reperfusion and clinical benefit, but only 2-5% of stroke patients receive tPA in the US. In part, this because tPA therapy unfortunately increases the risk of intracerebral hemorrhage by approximately 10-fold. Perhaps even more importantly, there is accumulating evidence from experimental models and clinical studies that tPA can have neurotoxic actions separate from its beneficial clot lysis properties, tPA neurotoxicity may further exacerbate ischemic brain damage, particularly in the 50% of patients who have no perfusion improvement after receiving intravenous tPA.

Many clinical trials attempting to provide neuroprotection following stroke have failed. While, to date, tPA-based thrombolytic therapy is the only FDA-approved treatment for achieving vascular reperfusion and clinical benefit, this agent is given to only about 2-5% of stroke patients (25, 26). This may be related, in part, to the elevated risks of symptomatic intracranial hemorrhage, and a short therapeutic time window in order to decrease the clinical risk of tPA's limitations. Specifically, tPA therapy limitations include: (1) short 3 hr treatment time window, (2) risk of intracerebral hemorrhage, and (3) neurotoxicity. Others have tried to find other lytics with equal thrombolysis properties for safe and effective reperfusion at longer times after stroke onset. One example is the vampire bat saliva molecule desmoteplase. However, the recent completion of a desmoteplase (DIAS-2) clinical trial failed. So the problem of a safe and effective use of tPA in the treatment of stroke remains unsolved.

What is needed is a composition and method that increases the thrombolytic efficacy of tPA, while reducing neurotoxicity and the risk of hemorrhagic transformation.

SUMMARY

The present invention is related to the field of vascular disorders. In particular, the present invention is related to the treatment and management of diseases including, but not limited to, stroke, myocardial infarction, deep vein thrombosis, or pulmonary embolism. For example, a patient having suffered a vascular disorder may be administered a composition comprising Annexin A2 and tPA. In such cases, the tPA dose may be reduced such that the risk of hemorrhagic side effects are minimal.

In one embodiment, the present invention contemplates a method comprising: a) providing: i) a patient exhibiting symptoms associated with a vascular disorder, and ii) a medium comprising Annexin A2 and tissue plasminogen activator (tPA); and b) administering said medium to said patient under conditions such that said symptoms are reduced. In one embodiment, the vascular disorder is selected from the group comprising stroke, myocardial infarction, pulmonary embolism, deep vein thrombosis or intracerebral hematoma. In one embodiment, the Annexin A2 and the tPA have a dose ratio of 2:1. In one embodiment, the medium comprises a carrier. In one embodiment, the Annexin A2 and the tPA are attached to the carrier. In one embodiment, the carrier is selected from the group comprising a liposome or a microparticle. In one embodiment, the medium comprises a liquid. In one embodiment, the administering is intravenous. In one embodiment, the patient is a human. In one embodiment, the patient is a non-human.

In one embodiment, the present invention contemplates a method comprising: a) providing: i) a patient exhibiting symptoms associated with a recently incurred stroke, ii) a medium comprising Annexin A2 and tissue plasminogen activator (tPA), wherein Annexin A2 and tPA have a dose ratio of 2:1; and, b) administering said medium to said human subject under conditions such that said symptoms are reduced. In one embodiment, the administering occurred less than three hours after said stroke. In one embodiment, the administering occurred less than six hours after said stroke. In one embodiment, the administering occurred less than twelve hours after said stroke. In one embodiment, the tPA dose is at least two-fold lower than the currently recommended dose. In one embodiment, the tPA dose is at least three-fold lower than the currently recommended dose. In one embodiment, the tPA dose is at least four-fold lower than the currently recommended dose.

In one embodiment, the present invention contemplates a medium comprising Annexin A2 and tissue plasminogen activator (tPA). In one embodiment, the Annexin A2 and the tPA have a dose ratio of 2:1. In one embodiment, the medium further comprises a carrier. In one embodiment, the Annexin A2 and the tPA are attached to the carrier. In one embodiment, the carrier comprises a liposome population. In one embodiment, the carrier comprises a microparticle population. In one embodiment, the medium comprises a liquid.

In one embodiment, the present invention contemplates a kit comprising a medium comprising Annexin A2 and tissue plasminogen activator (tPA). In one embodiment, the medium further comprises a carrier. In one embodiment, the tPA and the Annexin A2 are attached to said carrier. In one embodiment, the kit further comprises a sheet of instructions regarding administration of said medium following a vascular disorder. In one embodiment, the vascular disorder is selected from the group comprising stroke, myocardial infarction, pulmonary embolism, deep vein thrombosis or intracerebral hematoma. In one embodiment, the kit further comprises a syringe. In one embodiment, the kit further comprises an intravenous catheter. In one embodiment, the kit further comprises an intravenous drip bag capable of fluid communication with said intravenous catheter.

DEFINITIONS

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "medium" as used herein, refers to any material, or combination of materials, which may serve as vehicle for delivering of a drug, or carrier, to a treatment point (e.g., a thrombosis, a stenosis etc.). Preferably, a medium is selected from the group including, but not limited to, liquids, foams, or gels (including, but not limited to, hydrogels). In some cases a medium constitutes a drug delivery system that provides a controlled and sustained release of drugs over a period of time lasting approximately from 1 day to 6 months. Alternatively, the controlled and sustained drug release is from a carrier mixed within the medium.

The term "carrier" as used herein, refers to any material capable of attaching a drug or composition wherein a medium facilitates delivery of the carrier to a treatment point. Preferably, a carrier is selected from the group including, but not limited to, liposomes, xerogels, or microparticles (i.e., microspheres, liposomes, microcapsules etc.). Any carrier contemplated by this invention may comprise a controlled release formulation.

The term "xerogel" as used herein, refers to any device comprising a combination of silicone and oxygen having a plurality of air bubbles and an entrapped drug. The resultant glassy matrix is capable of a controlled release of an entrapped drug during the dissolution of the matrix.

The term "foam" as used herein, refers to a dispersion in which a large proportion of gas, by volume, is in the form of gas bubbles and dispersed within a liquid, solid or gel. The diameter of the bubbles are usually relatively larger than the thickness of the lamellae between the bubbles.

The term "gel" as used herein, refers to any material forming, to various degrees, a medium viscosity liquid or a jelly-like product when suspended in a solvent. A gel may also encompass a solid or semisolid colloid containing a certain amount of water. These colloid solutions are often referred to in the art as hydrosols. One specific type of gel is a hydrogel. The term "hydrogel" as used herein, refers to any material forming, to various degrees, a jelly-like product when suspended in a solvent, typically water or polar solvents comprising such as, but not limited to, gelatin and pectin and fractions and derivatives thereof. Typically, a hydrogel is capable of swelling in water and retains a significant portion of water within its structure without dissolution. In one embodiment, the present invention contemplates a gel that is liquid at lower than body temperature and forms a firm gel when at body temperature.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars. Drugs or compounds may have any of a variety of activities, which may be stimulatory or inhibitory, such as antibiotic activity, antiviral activity, antifungal activity, steroidal activity, cytotoxic, cytostatic, anti-proliferative, anti-inflammatory, analgesic or anesthetic activity, or can be useful as contrast or other diagnostic agents. Drugs or compounds may be capable of reducing thromboses and/or adhesions.

The term "administered" or "administering" a drug or compound, as used herein, refers to any method of providing a drug or compound to a patient such that the drug or compound has its intended effect on the patient. For example, one method of administering is by an indirect mechanism using a medical device such as, but not limited to a syringe, an intravenous catheter, etc. A second exemplary method of administering is by a direct mechanism such as, local tissue administration (i.e., for example, extravascular placement), oral ingestion, transdermal patch, topical, inhalation, suppository etc.

The term "biocompatible", as used herein, refers to any material does not elicit a substantial detrimental response in the host. There is always concern, when a foreign object is introduced into a living body, that the object will induce an immune reaction, such as an inflammatory response that will have negative effects on the host. In the context of this invention, biocompatibility is evaluated according to the application for which it was designed: for example; a bandage is regarded a biocompatible with the skin, whereas an implanted medical device is regarded as biocompatible with the internal tissues of the body. Preferably, biocompatible materials include, but are not limited to, biodegradable and biostable materials.

The term "local delivery" as used herein, refers to any drug or compound that is placed on or near a tissue surface without systemic distribution. The tissue surface includes, but is not limited to, the external skin or any internal tissue (i.e., for example, the periadvential blood vessel) and/or organ surface.

The term "antiplatelets" or "antiplatelet drug" as used herein, refers to any drug that prevents aggregation of platelets or fibrin formation (i.e., for example as a prior event to adhesion formation). For example, an antiplatelet drug comprises an inhibitor of glycoprotein IIb/IIIa (GPIIb/IIIa). Further a GPIIb/IIIa inhibitor includes, but is not limited to, xemilofiban, abciximab (ReoPro®) cromafiban, elarofiban, orbofiban, roxifiban, sibrafiban, RPR 109891, tirofiban (Agrastat®), eptifibatide (Integrilin®), UR-4033, UR-3216 or UR-2922.

The term, "antithrombins" or "antithrombin drug" as used herein, refers to any drug that inhibits or reduces thrombi formation and include, but are not limited to, bivalirudin, ximelagatran, hirudin, hirulog, argatroban, inogatran, efegatran, or thrombomodulin.

The term, "anticoagulants" or "anticoagulant drug" as used herein, refers to any drug that inhibits the blood coagulation cascade. A typical anticoagulant comprises heparin, including but not limited to, low molecular weight heparin (LMWH) or unfractionated heparin (UFH). Other anticoagulants include, but are not limited to, tinzaparin, certoparin, parnaparin, nadroparin, ardeparin, enoxaparin, reviparin or dalteparin. Specific inhibitors of the blood coagulation cascade include, but are not limited to, Factor Xa (FXa) inhibitors (i.e., for example, fondaparinux), Factor IXa (FIXa) inhibitors, Factor XIIIa (FXIIIa) inhibitors, and Factor VIIa (FVIIa) inhibitors.

The term "patient", as used herein, is a human or animal (i.e., for example, a dog, cat, horse, cow, pig etc.) and need not be hospitalized. For example, out-patients, persons in nursing homes are "patients." A patient may comprise any age of a human or non-human animal and therefore includes both adult and juveniles (i.e., children and/or offspring). It is not intended that the term "patient" connote a need for medical treatment, therefore, a patient may voluntarily or involuntarily be part of experimentation whether clinical or in support of basic science studies.

The term "medical device", as used herein, refers broadly to any apparatus used in relation to a medical procedure. Specifically, any apparatus that contacts a patient during a medical procedure or therapy is contemplated herein as a medical device. Similarly, any apparatus that administers a drug or compound to a patient during a medical procedure or therapy is contemplated herein as a medical device. "Direct medical implants" include, but are not limited to, urinary and intravascular catheters, dialysis catheters, wound drain tubes, skin sutures, vascular grafts and implantable meshes, intraocular devices, implantable drug delivery systems and heart valves, and the like. "Wound care devices" include, but are not limited to, general wound dressings, non-adherent dressings, burn dressings, biological graft materials, tape closures and dressings, surgical drapes, sponges and absorbable hemostats. "Surgical devices" include, but are not limited to, surgical instruments, endoscope systems (i.e., catheters, vascular catheters, surgical tools such as scalpels, retractors, and the like) and temporary drug delivery devices such as drug ports, injection needles etc. to administer the medium. A medical device is "coated" when a medium comprising a tPA and Annexin A2 becomes attached to the surface of the medical device (either directly or indirectly). Such an indirect attachment may result from coating a medical device with a polymer comprising the medium. This attachment may be permanent or temporary. When temporary, the attachment may result in a controlled release of a tPA/rA2 combination.

The term "dialysis/apheresis catheter" as used herein, refers to any multi-lumen catheter (i.e., for example, a triple lumen catheter) capable of providing a simultaneous withdrawal and return of blood to a patient undergoing a blood treatment process. Apheresis (called also pheresis) comprises a blood treatment process involving separation of blood elements that can remove soluble drugs or cellular elements from the circulation. Deisseroth et al., "Use Of Blood And Blood Products", Cancer: Principles And Practice Of Oncology, Devita, V. T. Jr. et al. Editors, Philadelphia: J. B. Lippincott Company 1989, p. 2045-2059. For example, blood is withdrawn from a donor, some blood elements (i.e., for example, plasma, leukocytes, platelets, etc.) are separated and retained. The unretained blood elements are then retransfused into the donor.

The term "dialysis catheter" as used herein, refers to any device capable of removing toxic substances (impurities or wastes) from the body when the kidneys are unable to do so. A dialysis catheter may comprise a single catheter having at least a dual lumen (i.e., one lumen withdraws arterial blood and a second lumen returns the dialyzed blood to the venous system) or involve placing two catheters-one that is placed in an artery, and one in an adjacent vein. Dialysis catheters are most frequently used for patients who have kidney failure, but may also be used to quickly remove drugs or poisons in acute situations.

The term "peritoneal dialysis catheter" as used herein, refers to any continuous flow catheters with at least two lumens, one of which is a short lumen (used to infuse a dialysis solution into the peritoneum), and the other of which is a long coiled lumen having a plurality of openings, generally located on the inside of the coil. It is believed that peritoneal solutes enter into the coiled lumen openings and are thereby removed from the peritoneum. One hypothesis suggests that peritoneal dialysis works by using the peritoneal membrane inside the abdomen as the semipermeable membrane. Special solutions that facilitate removal of toxins may be infused in, remain in the abdomen for a time, and then drained out.

The term "fixed split-tip dialysis catheter" as used herein, refers to any catheter having at least two distinct elongated end portions that extend substantially parallel to the longitudinal axis of the catheter and are flexible to the lateral displacement of an infused fluid. It is believed that this flexibility prevents a permanent catheter tip splay that is known to injure tissue. Usually a fixed-tip dialysis catheter provides indwelling vascular access for patients undergoing long-term renal dialysis care (i.e., for example, end-stage renal disease).

The term "femoral catheter" as used herein, refers to any catheter that is inserted into the femoral vein. Femoral catheters are typically provided for intermediate term blood access because the superior vena cava is relatively close to the right atrium of the heart, the minimal range of shape changes of these veins with natural movements of the patient (to minimize the damage to the vessel intima), and because of good acceptance by the patients of the skin exit on the thoracic wall. Further, the femoral veins are easy to cannulate, so that catheters of this invention may be inserted into the femoral veins at the bed side.

The term "endoscope" refers to any medical device that is capable of being inserted into a living body and used for tasks including, but not limited to, observing surgical procedures, performing surgical procedures, or applying medium to a surgical site. An endoscope is illustrated by instruments including, but not limited to, an arthroscope, a laparoscope, hysteroscope, cytoscope, etc. It is not intended to limit the use of an endoscope to hollow organs. It is specifically contemplated that endoscopes, such as an arthroscope or a laparoscope is inserted through the skin and courses to a closed surgical site.

The term, "microparticle" as used herein, refers to any microscopic carrier to which a drug or compound may be attached. Preferably, microparticles contemplated by this invention are capable of formulations having controlled release properties.

The term "PLGA" as used herein, refers to mixtures of polymers or copolymers of lactic acid and glycolic acid. As used herein, lactide polymers are chemically equivalent to lactic acid polymer and glycolide polymers are chemically equivalent to glycolic acid polymers. In one embodiment, PLGA contemplates an alternating mixture of lactide and glycolide polymers, and is referred to as a poly(lactide-co-glycolide) polymer.

The term "stenosis" is defined herein as referring to any narrowing of the internal diameter of a biological tissue, such as a vessel. In particular, such narrowing is caused by phenomenon including, but not limited to, arteriosclerosis, scar tissue and/or adhesions.

The term "restenosis" is defined herein as referring to any condition wherein "stenosis", having been treated and at least partially reversed, recurs.

The term "vascular access site" is defined herein as referring to any percutaneous insertion of a medical device into the vasculature. For example, a hemodialysis catheter placement comprises a vascular access site. Such sites may be temporary (i.e., placed for a matter of hours) or permanent (i.e., placed for days, months or years).

The term "syringe" or "catheter" as used herein, refers to any device or apparatus designed for liquid administration, as defined herein. A syringe or catheter may comprise at least one storage vessel (i.e., for example, a barrel) wherein a single medium resides prior to administration. A syringe or catheter comprising two or more barrels, each containing a separate medium, may mix the media from each barrel prior to administration or the media of each barrel may be administered separately. One of skill in the art will recognize that any catheter designed to perform dialysis, as defined herein, may also administer liquids.

The term "vascular graft" as used herein, refers to any conduit or portion thereof intended as a prosthetic device for conveying blood and, therefore, having a blood contacting surface (i.e., "luminal"). While usually in a tubular form, the graft may also be a sheet of material useful for patching portions of the circumference of living blood vessels (these materials are generally referred to as surgical wraps). Likewise, the term vascular graft includes intraluminal grafts for use within living blood vessels. The inventive grafts as such may also be used as a stent covering on the exterior, luminal or both surfaces of an implantable vascular stent.

The term "anti-thrombotic drug combination" as used herein, refers to any composition comprising at least one plasminogen activator (i.e., for example, tPA) and at least one Annexin protein (i.e., for example, recombinant Annexin A2; rA2). Other drugs including, but not limited to, antithrombin drugs, anticoagulant drugs or antiinflammatory drugs may also be in this combination.

The term "controlled release drug elution" as used herein, refers to any stable and quantifiable drug release from a polymer-based medium as contemplated herein.

The term "synthetic vascular graft" as used herein, refers to any artificial tube or cannula designed for insertion into a blood vessel. Such grafts may be constructed from polytetrafluoroethylene (PTFE).

The term "fibrin sheath" as used herein, refers to any encapsulation of a medical device subsequent to implantation. One hypothesis suggests that platelets and white blood cells respond to foreign substances in much the same way as an injured tissue (i.e., for example, a blood vessel) and that platelet adherence, followed by fibrin encapsulation, is involved in fibrin sheath formation.

The term "non-adhesive luminal surface" as used herein, refers to any vascular graft having been constructed, or treated, that prevents platelet attachment and subsequent thrombosis formation.

The term "currently recommended dose" as used herein, refers to the approved dosage established by a recognized regulatory body approving the administration of compounds to living being. For example, the Food & Drug Administration (FDA) approves dosages for human and non-human administration. For example, the FDA has approved the administration to humans of no more than 100 mg of tissue plasminogen activator (tPA: Activase®, Genentech) over the period of one hour.

The term "vascular disorder" as used herein, refers to any biochemical, physiological, structural, or anatomical abnormality occurring within the cardiovascular system. For example, such vascular disorders include, but are not limited to, stroke, myocardial infarction, deep vein thrombosis, pulmonary embolism, thrombophlebitis, or intracerebral hematoma.

The term "annexin" as used herein, refers to a family of highly homologous antithrombotic proteins believed to prevent both cellular and humoral amplification of platelet aggregation. It also may act as a "plasmin activator" such that when in contact with a plasminogen activator, the production of plasmin is increased.

The term "plasminogen activator" as used herein, refers to any compound (i.e., usually a protein) that is capable of converting plasminogen into plasmin (i.e., for example, tissue plasminogen activator (tPA) or urokinase-type plasminogen activator (uPA)).

The term "population" as used herein, refers to any mixture of particles (i.e., for example, liposomes or microparticles) having a distribution in diameter size. For example, a population of microparticles may range is particle diameter from between approximately 1-5000 μm, preferably between approximately 350-3500 μm, more preferably between approximately 1000-2000 μm.

The term "symptoms are reduced" as used herein, refers to a qualitative or quantitative reduction in detectable symptoms, including, but not limited to, a detectable impact on the rate of recovery from disease (e.g. rate of thrombus regression) or a detectable impact on the rate of development of disease (e.g., rate of thrombus growth).

The term "recently incurred" as used herein, refers to the onset of a particular vascular disorder within the past twelve hours. Preferably onset within the past six hours, but more preferably onset within the past four hours.

The term "a sheet of instructions" as used herein, refers to any method of means of storing and retrieving written or spoken information. Such instructions are preferably related to the use of a kit containing a therapeutic method contemplated herein. Such instructions may also provide information regarding interpretation of the results of the therapeutic method such that a clinical diagnosis can be reached.

BRIEF DESCRIPTION OF THE FIGURES

FIG. 1 presents exemplary data showing an effect of rA2 on tPA-dependent plasmain generation in vitro.

FIG. 2A demonstrates that two hours after initiation of ischemia, animals were treated intravenously with either saline, high dose tPA (10 mg/kg, H-tPA), intermediate dose tPA (5 mg/kg, M-tPA), low dose tPA (2.5 mg/kg, L-tPA), rA2 alone (5 mg/kg), or a combination of low dose tPA (2.5 mg/kg) plus rA2 (5 mg/kg). Laser doppler flowmetry was used to monitor regional cerebral blood flow (rCBF) for up to 1 h after treatment.

FIG. 2B demonstrates that at 24 hrs after stroke, brain infarction was stained by TTC, and the volume was quantified using computer-assisted image analysis. Data expressed as mean+s.e.m., *$P<0.05$ for L-tPA plus rAN, #$P<0.05$ for H-tPA, respectively, n=10 per group.

FIG. 3A. At 4 h after stroke onset, three groups of rats were treated intravenously with either saline, high dose tPA (10 mg/kg, H-tPA), or low dose tPA (2.5 mg/kg, L-tPA) plus rA2 (5 mg/kg). Shown here are representative images of brain sections after TTC staining at 24 h after initiating ischemia. Ischemic infarctions (white color area) were detected in all three groups, however large visible hemorrhage appeared only on the brain sections of H-tPA treated rats pointed by arrows.

FIG. 3B. At 24 h after stroke, brain infarction was quantified using computer-assisted image analysis.

FIG. 3C. Volumes of intracerebral hemorrhage ware quantified with hemoglobin assay at 24 h after stroke.

FIG. 3D. Hemispheric swelling rates were calculated from TITC stained brain slices. Data expressed as mean+s.e.m., *$P<0.05$, n=11 per group.

FIG. 4A. Effects of rA2 plus low dose tPA in fibrinolysis. Plasma samples were collected before ischemia (Pre-ischemia), just before thrombolytic therapy (Ischemia), and 1 h after treatment (Thrombolysis). Concentrations of fibrin degradation product D-dimer in plasma were quantified by ELISA analysis. Data expressed as mean+s.e.m., *P<0.01 versus ischemia, #P<0.01, n=6 per group.

FIG. 4B. Representative MR angiograms (MRA). rA2 (5 mg/kg) plus low dose tPA (2.5 mg/kg) was IV injected at 4 hr after stroke onset in embolic stroke rats. Time of flight (TOF) technique was used to assess cerebral vessel MRA imaging. It showed clear MCA occlusion examined at 3 hr after stroke (Before Thrombolysis), and clear recanalization at 1 hr after thrombolysis by the combination.

FIG. 4C. Representative cerebral blood flow (CBF) map (perfusion image). The map was obtained using a 2-coil continuous arterial spin labeling technique. On the same rat, CBF was significantly reduced at 3 hr after stroke (before thrombolysis) in the ipsilateral region, and a clear improvement in the same region at 1 hr after thrombolysis by given the combination. The CBF improving rate was 62.3% for rA2 plus low dose tPA versus 28.3% for high dose tPA alone (n=2).

FIG. 5 presents one embodiment of a human Annexin II protein sequence (A) (SEQ ID NO: 1) and corresponding nucleotide sequence (B) (SEQ ID NO: 2).

DETAILED DESCRIPTION

Figure 1A:
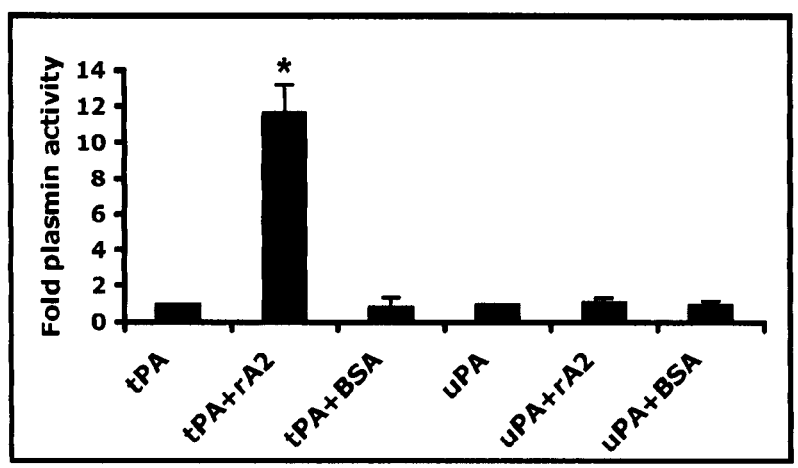
FIG. 1A demonstrates plasmin activity expressed as a ratio that generated by either 2.5 mg/ml of tPA alone or 100 Units/ml of uPA alone. Data were expressed as mean+s.e.m, *$P<0.001$, n=4 per group.

The present invention is related to the field of vascular disorders. In particular, the present invention is related to the treatment and management of diseases including, but not limited to, stroke, myocardial infarction, deep vein thrombosis, or pulmonary embolism. For example, a patient having suffered a vascular disorder may be administered a composition comprising tPA and Annexin A2. In such cases, the tPA dose may be reduced such that the risk of hemorrhagic side effects are minimal.

Hemorrhagic transformations, neurotoxicities and a short treatment time window include, but not limited to, some limitations for effective tPA stroke therapy. These limitations are related to the high dose of tPA required to generate the necessary amounts of plasmin sufficient for clot lysis. In one embodiment, the present invention contemplates that soluble Annexin A2 unexpectedly potentiates tPA-mediated plasmin generation in vitro, thereby resulting in improved reductions in in vivo thrombus formation. Although it is not necessary to understand the mechanism of an invention it is believed that a combination of Annexin A2 with tPA can significantly enhance thrombolysis efficacy, such that lower doses of tPA can be administered that avoid neurotoxic and hemorrhagic complications.

For example, after synthesis, purified recombinant human Annexin A2 protein was confirmed to provide Annexin A2-tPA induced in vitro amplification of plasmin generation. Using a rat embolic stroke model, a tPA-recombinant Annexin A2 protein combination was administered 2 hours after the ischemia-induced embolic stroke. The effective dose required for tPA to restore cerebral blood flow was reduced by 4-fold, also resulting in reduced brain infarctions. Further, the Annexin A2-tPA combination also prolonged the effective treatment time window to prevent thrombolysis (the currently accepted therapeutic window is limited to three hours post stroke event). For example, when compared to tPA (10 mg/kg) alone, the Annexin A2 (5 mg/kg)/tPA (2.5 mg/kg) (i.e., a 2:1 Annexin A2-tPA ratio) combination significantly enhanced fibrinolysis and reperfusion; attenuated mortality, brain infarctions, and hemorrhagic transformations, when administered at 4 hours post stroke event. These data show that when used in combination with recombinant Annexin A2, the effective thrombolytic dose of tPA can be decreased. As a result, brain hemorrhage and infarction can be reduced, and the therapeutic time window for stroke reperfusion prolonged.

Although it is not necessary to understand the mechanism of an invention it is believed that the molecular complex of tPA-Annexin A2-plasminogen amplifies tPA-converted plasmin generation in vitro and inhibits clot formation in vivo. For example, in the rat embolic model, a combination treatment at 2 hrs after stroke onset with low dose (2.5 mg/kg) plus Annexin A2 (5 mg/kg) showed similar therapeutic benefits as treatment with high dose (10 mg/kg) tPA alone in terms of restoring cerebral perfusion and reducing infarct volumes at 24 hrs. It is further shown that when treatment was delayed to four hrs after stroke onset, a tPA plus Annexin A2 combination treatment improved cerebral perfusion and reduced infarction without hemorrhagic transformation.

With the advantages of this invention, more ischemic stroke patients may be able to receive tPA treatments beyond the currently recommended three hour post-stroke event time window. As a result, it is expected that patients receiving a tPA/Annexin A2 combination treatment will have lower risk for intracerebral hemorrhage, and better clinic outcomes.

I. Tissue Plasminogen Activator (tPA)

Tissue plasminogen activator (tPA) is a fibrin-specific activator that converts plasminogen to plasmin. tPA stimulates thrombolysis and rescues the ischemic brain by restoring blood flow. However, emerging data suggest that besides clot lysis per se, exogenous tPA may have: i) pleiotropic actions in the brain (14); ii) direct vasoactivity (27); iii) cleavage of the N-methyl-D-aspartate (NMDA) NR1 subunit (28); and iv) activation of other extracellular proteases such as matrix metalloproteinases (MMPs) (3, 13, 28, 29). Further, these effects may increase neuronal excitotoxicity, further damage the blood brain barrier, and/or worsen edema and cerebral hemorrhage (14). Because of these shortcomings, there is a clinical need to develop new approaches that might increase thrombolytic efficacy with longer therapeutic time windows, reduce tPA-neurotoxicity and diminish the risk of hemorrhagic transformation. Combination therapies that can improve the benefit/risk ratio and lengthen treatment windows would make more patients eligible for tPA stroke therapy (30).

The above described shortcomings of using only tPA to treat stroke underscores that it is clinically and timely needed to identify new thrombolytics that might increase thrombolytic efficacy. Such an advance should also reduce tPA-neurotoxicity and the risk of hemorrhagic transformation, thereby improving the benefit/risk ratio for tPA stroke therapy.

In one embodiment, the present invention contemplates a composition capable of being administered using an effective tPA dose that is four times lower than currently recommended. Although it is not necessary to understand the mechanism of an invention it is believed that such a reduced dose reduces tPA-mediated side effects resulting from intracerebral hemorrhage and/or direct neurotoxicity. In one embodiment, the present invention contemplates a composition comprising a combination of tPA and recombinant human Annexin A2, wherein plasmin generation is amplified. Although it is not necessary to understand the mechanism of an invention it is believed that such plasmin generation will improve perfusion and provide greater clinical benefits. In one embodiment, the present invention contemplates a method comprising administering a composition comprising tPA and Annexin A2 to a patient more than three hours after a stroke event, and under conditions such that effective treatment is provided. Although it is not necessary to understand the mechanism of an invention it is believed that because Annexin A2 is an endogenous human protein a combined treatment with tPA may reduce the risk of an immune response.

The present embodiments identify new strategies that can increase the thrombolytic efficacy of tPA, while reducing its associated neurotoxicity and hemorrhagic transformation (1-6). Successful clot lysis for stroke therapy has required high doses of tPA, but it is well accepted that this practice increases the risk of intracerebral hemorrhage (7-9). Emerging evidence from experimental models and clinical studies demonstrates that tPA administered systemically can enter both normal and injured brain parenchyma (10, 11). Moreover, exogenous tPA can have neurotoxic actions that are not related to any clot lysis properties (12-15). Also, it has been reported that tPA mediated neurotoxicity may exacerbate ischemic damage, particularly to the about 50% of patients who have poor improvement in perfusion after receiving intravenous tPA (14).

Other studies have attempted to develop new approaches for tPA combination therapy in animal stroke models. For instance, the EEIIMD hexapeptide corresponding to amino acids 350-355 of plasminogen activator inhibitor type 1 abolished the tPA-induced increases in infarct size and intracranial bleeding in both mechanical and embolic models of stroke in rats (4). Co-treatment with tPA plus MMP inhibitors ameliorated reperfusion injury in a focal stroke model in rats (34), and also reduced the incidence of tPA-induced hemorrhage in rabbits (35). Reduced brain infarction and/or hemorrhage and thrombolytic window extension have been reported using combinations of tPA with: i) bortezomib (a potent and selective inhibitor of the proteasome) (36); ii) a glycoprotein IIb/m a receptor antagonist (37); iii) an antioxidant (2, 38); and iv) activated Protein C (39). Further, a rat model was used to test treatment with neuroserpin and recombinant human tPA. This combination resulted in reduced blood brain barrier leakage, brain edema and ischemic lesion volume as compared to treatment with tPA alone. Zhang et al., "Adjuvant Treatment with Neuroserpin Increases the Therapeutic Window for Tissue-Type Plasminogen Activator Administration in a Rat Model of Embolic Stroke" *Circulation* 106:740-745 (2002).

Finally, another recent study suggested that stabilization of mast cells with cromoglycate results in a significant reduction in tPA-mediated hemorrhage and reperfusion injury following focal cerebral ischemia in rats (40). Such a wide variety of experimental data only show that many mechanisms may contribute to the deleterious effects of tPA. All above experimental findings support the novelty of some embodiments of this invention contemplating that a lower tPA dose will reduce dose-related side effects, and enhance thrombolytic efficacy and/or safety.

II. Annexin A2

Annexin A2 (also known as Annexin II) is a calcium- and phospholipid-binding protein that serves as a pro-fibrinolytic co-receptor for tPA and plasminogen on endothelial cells (16, 17). Annexin A2 accelerates the activation of the clot-dissolving protease plasmin by complexing with tPA and with the plasmin precursor plasminogen which binds on endothelial cell surface and exist in the clot (18, 19). Although initially identified as an intracellular protein, Annexin A2 is also transported to the extracellular environment, and exists as both soluble and membrane-bound protein. Annexin A2 can be detected in human plasma and can be transported to the cell surface in response to cellular stress (33). Recent reports have demonstrated that soluble Annexin A2 not only dramatically increases tPA-dependent plasmin generation in vitro, but also reduces thrombus formation in rat carotid arteries and middle cerebral arteries in vivo (20, 21, respectively).

In one embodiment, the present invention contemplates a recombinant human Annexin A2 having a tPA binding site. In one embodiment, the present invention contemplates a tPA peptide is bound to the Annexin A2 peptide. In one embodiment, the binding site is modified to provide a high affinity tPA binding site.

In one embodiment, the present invention contemplates a recombinant human Annexin A2 having a plasmin binding site. In one embodiment, the present invention contemplates a plasmin peptide is bound to the Annexin A2 peptide. In one embodiment, the binding site is modified to provide a high affinity plasmin binding site.

The use of annexin proteins, including Annexin A2, for the treatment of thrombosis without increasing the risk of hemorrhaging has been reported. For example, Annexin A2 may be linked with the Fc portion of an immunoglobulin. However, this administration of Annexin A2 is advocated for administration in a "heterotetramer" form. Modified Annexin A2 proteins, including recombinant proteins, were suggested to prevent transient ischemic attacks from developing into full blown strokes (i.e., a preventative therapy). Combinations of Annexin A2 with tPA were not suggested, and in fact the disadvantages of tPA (i.e., increased bleeding risk) were pointed out tending to teach away from the presently contemplated embodiment. Allison, "Modified Annexin Proteins and Methods for Preventing Thrombosis," U.S. Pat. No. 6,962,903 (herein incorporated by reference). Annexin A2 has also been proposed as an effective therapeutic to reduce hemorrhaging when administered following retinal trauma and other ophthalmological disorders. Rich, "Methods of Stabilizing Hyaluronidase with Annexin A2," U.S. Pat. No. 7,115,408 (herein incorporated by reference).

III. Annexin A2 and tPA Combination Treatments

In one embodiment, the present invention contemplates that Annexin A2 may be therapeutically administered with tissue plasminogen activator (tPA) for treatment following a stroke. The present invention addresses current problems associated with the fact that tPA is currently the only FDA approved medicine for the generation of vascular reperfusion in stroke patients but relatively few patients actually receive tPA due to the increased risk of intracerebral hemorrhaging. In one embodiment, the present invention contemplates that Annexin A2, an endogenous protein of human plasma, may be combined in treatment regimens with tPA such that lower, non-neurotoxic dosages of tPA may be administered. Although it is not necessary to understand the mechanism of an invention it is believed that the dose of tPA may be reduced at least four-fold from currently recommended dosages when administered in combination with Annexin A2 a still achieve similar therapeutic effectiveness. Since tPA is broadly used in treating a range of thrombotic disorders, besides acute ischemic stroke, this new combination approach for lowering the minimum effective tPA dose may potentially improve tPA treatments for other conditions such as acute myocardial infarction, pulmonary embolism, deep venous thrombosis, thrombosed medical devices (i.e., for example, intravenous catheters), and lysis of intracerebral hematomas.

Specific advantages of a combination of tPA and Annexin A2 is that, tPA's associated risks when administered alone and at a high dose (i.e., for example, rat brain hemorrhaging after a 10 mg/kg dose) may be alleviated and/or avoided. Other embodiments contemplated by the present invention are that tPA/Annexin A2 combination therapies may further improve treatment outcomes for other medical conditions including, but not limited to, myocardial infarction, pulmonary embolism, deep vein thrombosis and lysis for intracerebral hematoma.

Although it is not necessary to understand the mechanism of an invention, it is believed that a combination of Annexin A2 and tPA can significantly enhance thrombolytic efficacy so that lower doses of tPA can be applied in ischemic stroke to avoid neurotoxic and hemorrhagic complications. The data presented herein demonstrate that this novel approach successfully achieved improvements in perfusion and brain tissue protection. Further, the risk of intracerebral hemorrhage was also significantly reduced. It is further believed that these beneficial effects on blood flow, infarct volume, hemorrhage and mortality suggest that rA2 might safely augment the efficacy and lengthen the treatment window of tPA stroke therapy.

Administered doses for a tPA and rA2 in vivo combination was based on in vitro plasmin generation data. The in vitro data indicated that an rA2/tPA combination at a 2:1 ratio increases the plasmin-generating capability of tPA by almost four-fold. The thrombolytic profiles may be evaluated by examining plasma levels of a fibrin degradation product, D-dimer. The assay is based upon degradation of cross-lined fibrin (enriched in fibrin thrombi) that produces a number of fragments containing the D-dimer epitope. The released D-dimer epitope is then utilized as an indicator the extent of fibrin clot lysis by ELISA. ELISA data showed that low dose tPA plus rA2 significantly increased D-dimer levels by about 2.9 fold compared to either saline or tPA alone.

A. Annexin A2-tPA Relationships

Annexin A2 has been reported to be the putative human endothelial tPA cell surface receptor. This relationship has resulted in broad speculation that the Annexin A2-tPA relationship may play a role in hemostasis and thrombosis. Hajjar et al., "An Endothelial Cell Receptor for Plasminogen/Tissue Plasminogen Activator" *Journal of Biological Chemistry* 269:21191-21197 (1994). Other, in vitro studies, have shown that Annexin A2 is capable of binding both plasmin and plasminogen in human endothelial cells and suggest that Annexin A2 may act as a catalyst for the activation of plasminogen by tPA. Hajjar et al., "Annexin A2: A Mediator of the Plasmin/Plasminogen Activator System, Trends in Cardiovascular Medicine" 9:128-138 (1999). However, until the presently disclosed invention, the therapeutic usefulness of providing a combination therapy of Annexin A2 and tPA has not been proposed.

Annexin A2-plasminogen activator combinations have been used for the treatment of other diseases. For example, an anti-angiogenic plasmin fragment and an Annexin A2 heterotetramer was reported to affect angiogenesis. In one combination used to effect angiogenesis, an Annexin A2 heterotetramer was combined with a urokinase-type plasminogen activator; an enzyme that interacts with tPA. Novokhatny et al., "Tissue-type plasminogen activator (tPA) interacts with urokinase-type plasminogen activator (uPA) via tPA's lysine binding site. An explanation of the poor fibrin affinity of recombinant tPA/uPA chimeric molecules" *Journal of Biological Chemistry* 270:8680-8685 (1995). The urokinase-type plasminogen activator-tPA (uPA) interaction in regards to angiogenesis, however, was not linked to Annexin A2 to provide an effective combination for the treatment of stroke. Waisman et al. "Anti-Angiogenesis Methods, Compositions and Uses Therefor," U.S. Pat. No. 7,250,271 (herein incorporated be reference). Further, while tPA is believed to stimulate plasmin production, there are those in the art that believe glycation of Annexin A2 may impair the appropriate formation of the plasminogen/tPA/Annexin A2 complex. Ribo et al. "Acute Hyperglycemia State is Associated with Lower tPA-Induced Recanalization Rates in Stroke Patients" *Stroke* 36:1705-1709 (2005). This evidence suggests that Annexin A2 and tPA have counterbalancing physiological roles, thereby arguing against an effective combination therapy.

B. rA2 Amplifies tPA-Mediated Plasmin Generation In Vitro

Figure 1B:
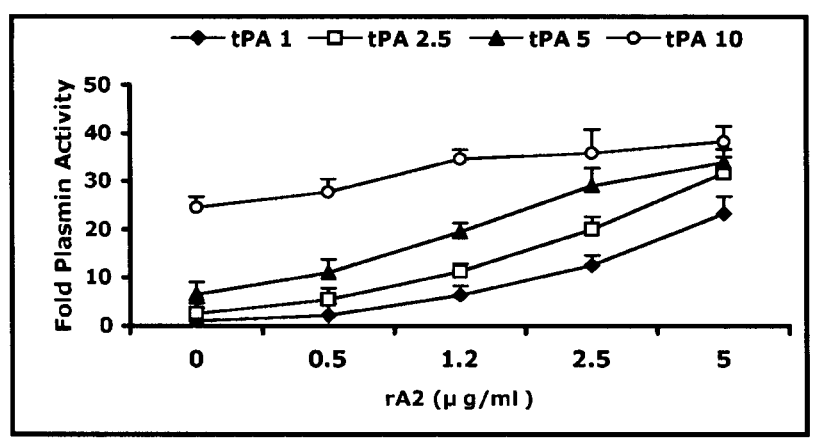
FIG. 1B demonstrates a range of concentrations of tPA (1, 2.5, 5, 10 mg/ml) plus/without the indicated concentrations of rA2 (0, 0.5, 1.2, 2.5, 5 mg/ml). Plasmin activity is represented as fold of plasmin activity related to 1 mg/ml of tPA alone. Data were expressed as mean+s.e.m., n=4 per group.

Recombinant human Annexin A2 protein (rA2) was synthesized in accordance with Example I and purified by SDS-PAGE and confirmed using a Western Blot (data not shown). In vitro plasmin activity assays showed a combination of rA2 (5 µg/ml) and tPA (2.5 µg/ml) significantly amplified tPA-converted plasmin generation. This amplification was Annexin A2-tPA specific because a combination of BSA protein (5 µg/ml) and tPA or a combination of rA2 and uPA did not increase plasmin activity. See, FIG. 1A. Further, a combination of rA2 and tPA significantly amplified tPA-converted plasmin generation in a dose-dependent manner. The data demonstrate that equal plasmin activity levels can be reached by either: i) a high dose tPA alone (clinically associated with cerebral hemorrhage); or ii) different rA2/tPA combinations having lower doses of tPA, such as: i) tPA 5 µg/ml (alone) versus a tPA (1 µg/ml)/rA2 (2.5 µg/ml) combination; or ii) tPA 10 µg/ml (alone) versus a tPA (2.5 µg/ml)/rA2 (5 µg/ml) combination. These data indicate that by combining rA2 with tPA at approximately a 2:1 w/v ratio (or alternatively, 4:1 molar ratio) increased the in vitro plasmin-generating capability of tPA by almost four-fold in vitro. See, FIG. 1B.

C. rA2 Decreases the Dose of tPA for Focal Embolic Stroke

It has been suggested that species differences may exist in fibrin specificities (22). Consequently, the equivalent effective dose of human recombinant tPA used in rat embolic stroke model studies is usually about 10 mg/kg, whereas an approximate 10 times higher dose is used in human clinical treatment.

Therefore, two hours after initiation of ischemia (i.e., for example, by clot infusion) rats were intravenously administered with either i) saline; ii) a high dose tPA (10 mg/kg); iii) an intermediate dose tPA (5 mg/kg); iv) a low dose tPA (2.5 mg/kg); v) rA2 alone (5 mg/kg); or vi) a combination of low dose tPA (2.5 mg/kg) plus rA2 (5 mg/kg).

Figure 2:
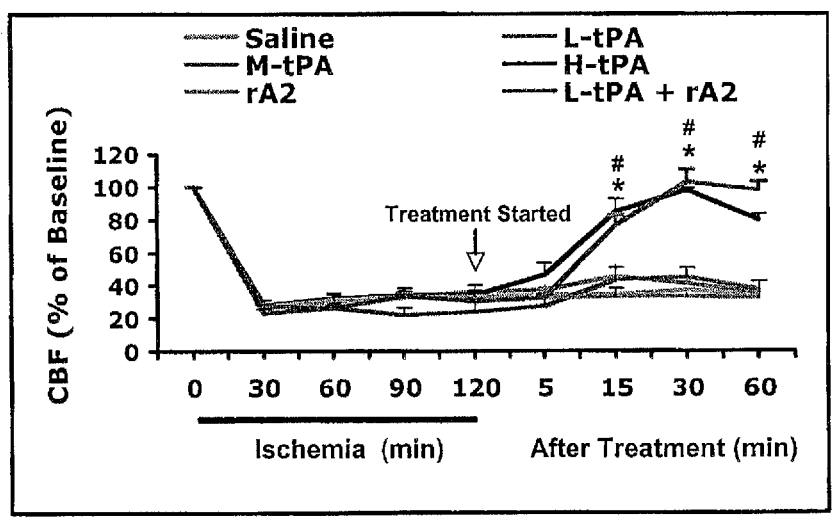
FIG. 2 presents exemplary data showing an effect of treating rats at 2 hrs after initiation of cerebral ischemia.
Figure 2:
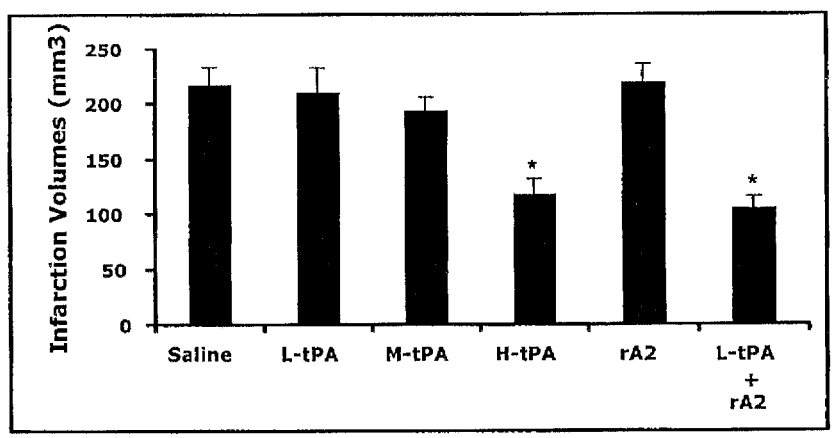

Laser doppler flowmetry was then used to monitor regional cerebral blood flow (rCBF) for up to 1 h after treatment. Brain infarction volume was quantified at 24 h after stroke. As expected, high dose tPA (10 mg/kg) induced almost complete reperfusion, and also decreased infarct volumes by about 45%. It should be noted that neither the intermediate dose tPA or the low dose tPA (alone), nor the rA2 dose (alone) were effective in improving reperfusion and reducing infarction. Surprisingly, the combination of low dose tPA and rA2 dose successfully achieved similar reperfusion and reduced infarct size as observed with high dose tPA (alone). See, FIG. 2A and FIG. 2A.

These data suggest that this combination is pharmacologically more effective and specific for fibrin clot lysis than currently recommended treatments (24). Further, the data supports embodiments of the present invention by providing improved therapy based upon plasmin-dependent fibrinolysis. Consequently, intravenous injection of a combination of 2.5 mg/kg tPA and 5 mg/kg rA2 may generate plasmin in equal or even greater amounts than 10 mg/kg tPA alone. This conclusion is consistent with the almost 100% rCBF recovery in the 2 h treatment protocols (supra), and the significant improvement in reperfusion even in rats treated at the delayed 4 h time point (infra). Although it is not necessary to understand the mechanism of an invention, it is believed that such increased efficiency of fibrinolysis by the A2-tPA combination might even generate more plasmin locally in the clot site. Previous findings have demonstrated that Annexin A2 accelerates the activation of plasmin by complexing with tPA and with the plasmin precursor plasminogen, which binds the endothelial cell surface and is enriched in the clot (19, 31). Therefore, a combination of tPA and recombinant Annexin A2 might locally bind plasminogen and consequently amplify plasmin generation in the vicinity of the clot, thereby resulting in more locally effective fibrinolysis.

D. Extension of the Thrombolytic Time Window

Previous studies using a rat model of embolic focal cerebral ischemia have shown that tPA treatment is effective only when given within 2-3 h after a stroke event (23). In one embodiment, the present invention contemplates a method wherein a combination therapy with tPA plus rA2 prolongs the conventional thrombolytic time window.

Figure 3:
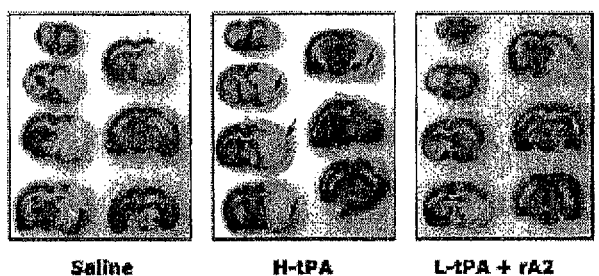
FIG. 3 presents exemplary data showing an effect of treating rats at 4 hrs after initiation of ischemia.
Figure 3:
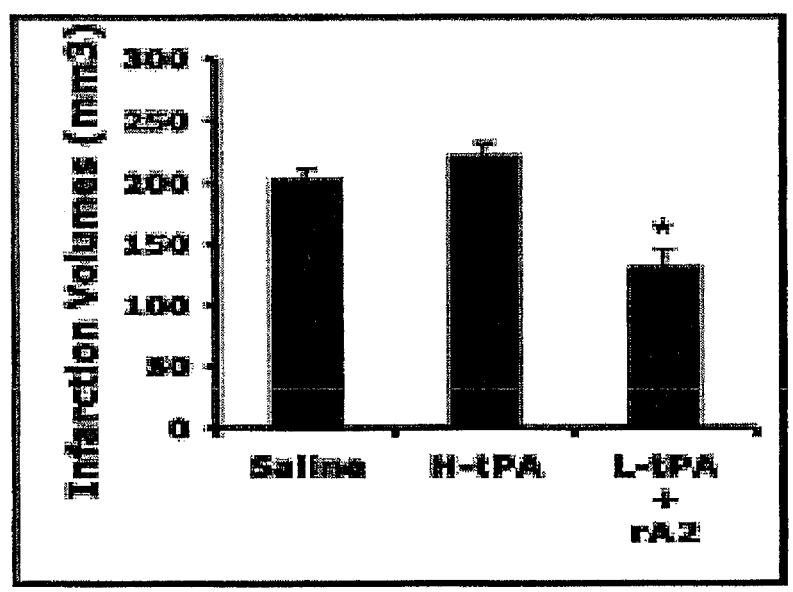
Figure 3:
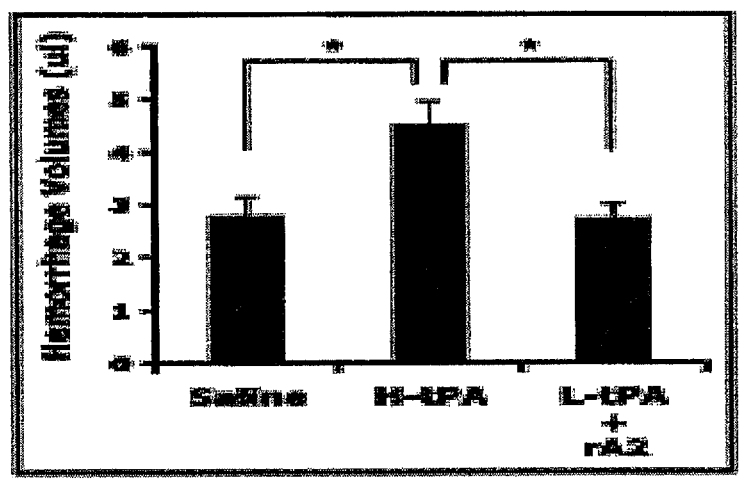
Figure 3:
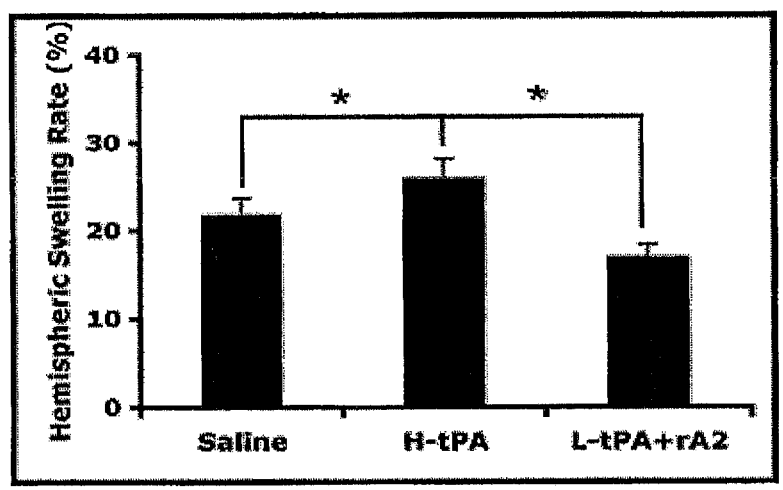

For example, at 4 hours after stroke onset, three groups of rats were treated intravenously with either saline, high dose tPA (10 mg/kg), or a combination of low dose tPA (2.5 mg/kg) and rA2 (5 mg/kg). At 24 h after initiation of stroke, this combination significantly reduced infarction volume, compared with either saline controls or rats treated with high-dose-tPA alone. See FIG. 3A, 3B. As expected, high dose tPA administered at the delayed 4 h time point induced significant hemorrhagic transformation at 24 h. This combination significantly ameliorated the severity of hemorrhagic transformation and hemispheric swelling. See FIG. 3C, 3D.

Finally, in concert with these beneficial effects on cerebral perfusion, infarction and hemorrhage, combination therapy of low-dose tPA plus rA2 also reduced mortality. Mortality rates were 29% in untreated rats and 41% in the high dose tPA group, whereas combination therapy with low dose tPA plus rA2 significantly reduced mortality to 15%. See, Table 1.

TABLE 1

Mortality Rates

| Groups | Saline | H-tPA | L-tPA + rA2 |
| --- | --- | --- | --- |
| Tested Animals | 14 | 17 | 13 |
| Dead Animals | 4 | 7 | 2 |
| Mortality % | 29 | 41 | 15 |

For the animals treated at 4 h after the initiation of stroke, the mortality rate of each group for the first 24 h are shown.
Combination treatment significantly eliminated the mortality related to H-tPA treatment.

In addition, physiological parameters measured before ischemia, after ischemia, and 30 min following thrombolysis remained within normal range in all groups. See, Table 2.

TABLE 2

Measurements of Physiological Parameters

| | Saline | H-tPA | L-tPA + rA2 |
| --- | --- | --- | --- |
| Weight (g) | 291 ± 7.91 | 287 ± 6.17 | 295 ± 8.22 |
| Rectal Temperature (° C.) | 37.1 ± 0.23 | 37.0 ± 0.13 | 36.8 ± 0.28 |
| MABP (mmHg) | 123 ± 4.23 | 120 ± 3.05 | 121 ± 4.21 |
| pH | 7.36 ± 0.04 | 7.41 ± 0.04 | 7.38 ± 0.05 |
| $PCO_2$ (mmHg) | 39.5 ± 2.87 | 39.8 ± 3.66 | 40.1 ± 4.24 |
| $PO_2$ (mmHg) | 125 ± 4.7 | 127 ± 4.8 | 126 ± 4.6 |

Physiological parameters were measured at 30 min after thrombolysis at 4 h after onset of stroke. All measurements remained within normal range in three groups. Mean ± S.E.M.

In some embodiments, the presently contemplated invention demonstrates that addition of a "plasmin amplifier" such as rA2 can decrease the effective thrombolytic dose of tPA, thereby reducing hemorrhage and brain infarction, and prolonging the reperfusion time window for stroke.

E. Fibrin Degradation Product D-Dimer

Figure 4:
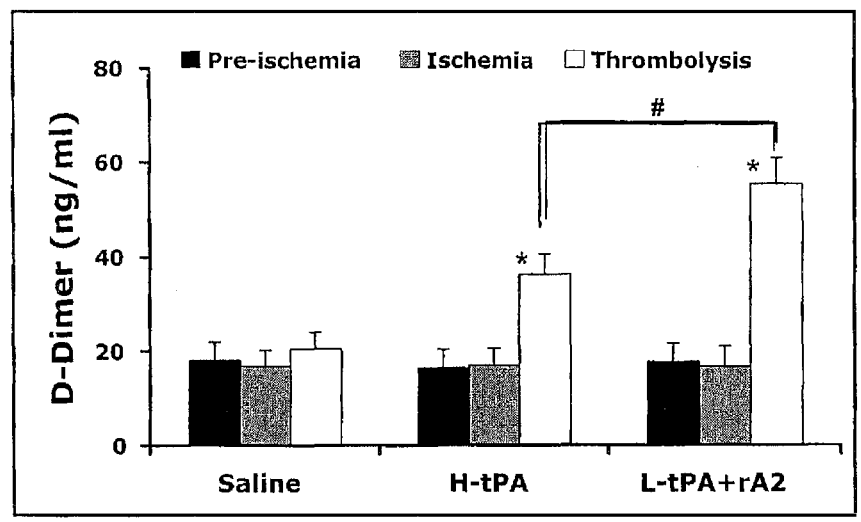
FIG. 4 present exemplary data showing an effect of tPA along or in combination with rA2 on fibrinolysis, and reperfusion improvement.
Figure 4:
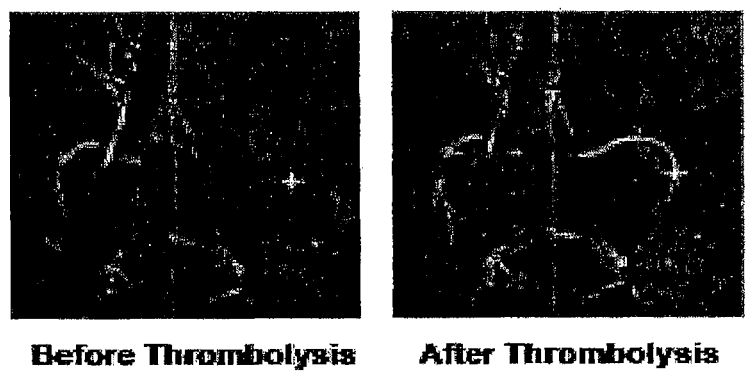
Figure 4:
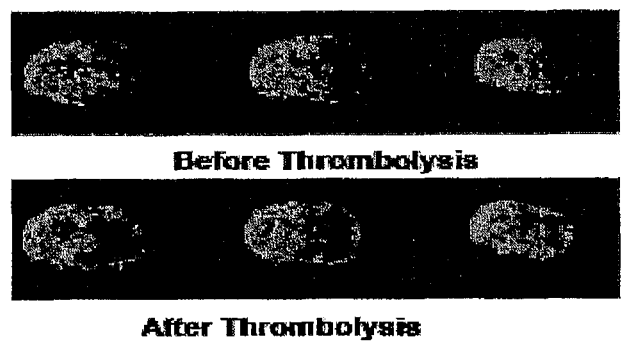

Plasma levels were examined of the fibrin degradation product D-dimer, a biomarker for fibrinolysis. ELISA data showed both high dose tPA and low dose tPA plus rA2 significantly increased D-dimer after thrombolysis for 2.2-fold and 3.2-fold, respectively, and the increase in low dose tPA plus rA2 combination was significantly greater compared to high dose tPA-only treatment. See, FIG. 4A. These data indicate that this combination thrombolytic therapy was more effective and specific for fibrinolysis than tPA along in delayed 4 hrs treatment (24).

F. MRI Reperfusion Imaging

Our initial MRI analysis also indicated the reperfusion improvement by the combination in the delayed 4 hrs treatments. See, FIG. 4B, 4C.

IV. Clinical Applications

In one embodiment, the present invention contemplates administering a rA2/tPA composition for the treatment of a vascular disorder. In one embodiment, the disorder may comprise a stroke. In one embodiment, the disorder may comprise a thrombosis. In one embodiment, the thrombosis may be attached to a medical device. In one embodiment, the disorder may comprise an embolism.

A. Stroke

Each year, about 600,000 Americans suffer from stroke. Thrombolytic therapy with tPA is the only FDA-approved medicine for achieving both vascular reperfusion and clinical benefit, but only 2-5% of stroke patients receive tPA in the US. In part, this because tPA therapy unfortunately increases the risk of intracerebral hemorrhage by approximately 10-fold. Perhaps even more importantly, there is accumulating evidence from experimental models and clinical studies that tPA can have neurotoxic actions separate from its beneficial clot lysis properties. tPA neurotoxicity may further exacerbate ischemic brain damage, particularly in the 50% of patients who have no perfusion improvement after receiving intravenous tPA. The present invention contemplates increasing the thrombolytic efficacy of tPA, while reducing neurotoxicity and the risk of hemorrhagic transformation. Although it is not necessary to understand the mechanism of an invention, it is believed that Annexin A2 will lower the dose of tPA required to generate plasmin thereby allowing the use of lower non-neurotoxic doses of tPA and also extending the treatment time window without incurring risks of brain hemorrhage.

1. Ischemic Strokes

Approximately eighty percent of strokes may be caused by too little blood reaching an area of the brain, which is usually due to a clot that has blocked a blood vessel (i.e., for example, a cerebral thrombosis). This is called "ischemic stroke." This type of stroke can sometimes lead to a brain hemorrhage because the affected brain tissue softens and this can lead to breaking down of small blood vessels. In addition, brain hemorrhage can occur when people have problems forming blood clots. Clots, which are the body's way of stopping any bleeding, are formed by proteins called coagulation factors and by sticky blood cells called platelets. Whenever the coagulation factors or platelets do not work well or are insufficient in quantity, people may develop a tendency to bleed excessively.

Ischemic strokes may be preceded by transient ischemic attacks (TIA), and it is estimated that about 300,000 persons suffer a TIA every year in the United States. It would be desirable to have a safe and effective agent that could be administered as a bolus and would for several days prevent recurrence of cerebral thrombosis without increasing the risk of cerebral hemorrhage. Thrombosis also contributes to peripheral arterial occlusion in diabetics and other patients, and an efficacious and safe antithrombotic agent for use in such patients is needed.

2. Hemorrhagic Strokes

Approximately twenty percent of strokes may involve bleeding within the brain, which damages nearby brain tissue (i.e., for example, a hemorrhagic stroke). Hemorrhagic stroke occurs when a blood vessel bursts inside the brain. The brain is very sensitive to bleeding and damage can occur very rapidly, either because of the presence of the blood itself, or because the fluid increases pressure on the brain and harms it by pressing it against the skull. Bleeding irritates the brain tissue, causing swelling. The surrounding tissues of the brain resist the expansion of the bleeding, which is finally contained by forming a mass (i.e., for example, an intracerebral hematoma). Both swelling and hematoma will compress and displace normal brain tissue. Most often, hemorrhagic stroke is associated with high blood pressure, which stresses the artery walls until they break.

One cause of hemorrhagic stroke is an aneurysm. This is a weak spot in an artery wall, which balloons out because of the pressure of the blood circulating inside the affected artery. Eventually, it can burst and cause serious harm. The larger the aneurysm is, the more likely it is to burst.

3. Symptomology

Stroke symptoms are typically of sudden onset and may quickly become worse. Stroke symptoms may include, but are not limited to: i) Weakness or inability to move a body part; ii) Numbness or loss of sensation; iii) Decreased or lost vision (may be partial); iv) Speech difficulties; v) Inability to recognize or identify familiar things; vi) Sudden headache; vii) Vertigo; viii) Dizziness; xi) Loss of coordination; x) Swallowing difficulties; and xi) Sleepy, stuporous, lethargic, comatose, and/or unconscious.

A stroke event may be detected by using a neurologic exam, which would be expected to show abnormal results. Further, a patient may look drowsy and confused. An eye examination may show abnormal eye movements, and changes may be seen upon retinal examination (examination of the back of the eye with an instrument called ophthalmoscope). The patient may also have abnormal reflexes. A computerized tomography scan will confirm the presence of a brain hemorrhage by providing pictures of the brain. A brain magnetic resonance imaging (MRI) scan can also be obtained later to better understand what caused the bleeding. A conventional angiography (i.e., for example, an X-ray of the arteries using dye) may be required to identify aneurysms or AVM. Other tests may include, but are not limited to: complete blood count, bleeding time, prothrombin/partial thromboplastin time (PT/PTT), and CSF (cerebrospinal fluid) examination.

B. Thromboses

Thrombosis may be defined as the formation, development, or presence of a blood clot (i.e. for example, a thrombus) in a blood vessel and is believed to be a common severe medical disorder. Thromboses may be involved in the generation of a variety of vascular disorders including, but not limited to, myocardial infarctions, cardiac ischemia, and/or deep vein thrombosis.

1. Myocardial Infarction

The most frequent example of arterial thrombosis is coronary thrombosis, which leads to occlusion of the coronary arteries and often to myocardial infarction (heart attack). More than 1.3 million patients are admitted to the hospital for myocardial infarction each year in North America. The standard therapy is administration of a thrombolytic protein by infusion. Thrombolytic treatment of acute myocardial infarction is estimated to save 30 lives per 1000 patients treated; nevertheless the 30-day mortality for this disorder remains substantial (Mehta et al., Lancet 356:449-454 (2000), incorporated herein by reference). It would be convenient to administer antithrombotic and thrombolytic agents by bolus injection, since they might be used before admission to hospital with additional benefit (Rawles, J. Am. Coll. Cardiol. 30:1181-1186 (1997), incorporated herein by reference). However, bolus injection (as opposed to a more gradual intravenous infusion) significantly increases the risk of cerebral hemorrhage (Mehta et al., 2000). The development of an agent able to prevent thrombosis and/or increase thrombolysis, without augmenting the risk of bleeding, would be desirable.

2. Cardiac Ischemia

Unstable angina, caused by inadequate oxygen delivery to the heart due to coronary occlusion, is the most common cause of admission to hospital, with 1.5 million cases a year in the United States alone. When patients with occlusion of coronary arteries are treated with angioplasty and stenting, the use of an antibody against platelet GP IIb/IIIa decreases the likelihood of restenosis. However, the same antibody has shown no benefit in unstable angina without angioplasty, and a better method for preventing coronary occlusion in these patients is needed.

3. Deep Vein Thrombosis

Deep venous thrombosis is a frequent complication of surgical procedures such as hip and knee arthroplasties. It would be desirable to prevent thrombosis without increasing hemorrhage into the field of operation. Similar considerations apply to venous thrombosis associated with pregnancy and parturition. Some persons are prone to repeated venous thrombotic events and are currently treated by antithrombotic agents such as coumarin-type drugs. The dose of such drugs must be titrated in each patient, and the margin between effective antithrombotic doses and those increasing hemorrhage is small. Having a treatment with better separation of antithrombotic activity from increased risk of bleeding is desirable. All of the recently introduced antithrombotic therapies, including ligands of platelet GP IIb/IIIa, low molecular weight heparins, and a pentasaccharide inhibitor of factor Xa, carry an increased risk of bleeding (Levine et al., Chest 119: 108 S-121S (2001), incorporated herein by reference). Hence there is a need to explore alternative strategies for preventing arterial and venous thrombosis without augmenting the risk of hemorrhage.

Deep vein thrombosis may be detected by tests including, but not limited to: i) Doppler ultrasound exam of an extremity blood flow studies; ii) Venography of the legs; or iii) Plethysmography of the legs.

To inhibit the extension of arterial or venous thrombi without increasing hemorrhage, it is necessary to exploit potential differences between mechanisms involved in hemostasis and those involved in thrombosis in large blood vessels. Primary hemostatic mechanisms include the formation of platelet microaggregates, which plug capillaries and accumulate over damaged or activated endothelial cells in small blood vessels. Inhibitors of platelet aggregation, including agents suppressing the formation or action of thromboxane $A_2$, ligands of GP IIa/IIIb, and drugs acting on ADP receptors such as clopidogrel (Hallopeter, Nature 409:202-207 (2001), incorporated herein by reference), interfere with this process and therefore increase the risk of bleeding (Levine et al., 2001). In contrast to microaggregate formation, occlusion by an arterial or venous thrombus requires the continued recruitment and incorporation of platelets into the thrombus. To overcome detachment by shear forces in large blood vessels, platelets must be bound tightly to one another and to the fibrin network deposited around them.

Evidence has accumulated that the formation of tight macroaggregates of platelets is facilitated by a cellular and a humoral amplification mechanism, which reinforce each other. In the cellular mechanism, the formation of relatively loose microaggregates of platelets, induced by moderate concentrations of agonists such as ADP, thromboxane $A_2$, or collagen, is accompanied by the release from platelet-α-granules of the 85-kD protein Gas6 (Angelillo-Scherrer et al., Nature Medicine 7:215-221 (2001), incorporated herein by reference). Binding of released Gas6 to receptor tyrosine kinases (Axl, Sky, Mer) expressed on the surface of platelets induces complete degranulation and the formation of tight macroaggregates of these cells. In the humoral amplification mechanism, a prothrombinase complex is formed on the surface of activated platelets and microvesicles. This generates thrombin and fibrin. Thrombin is itself a potent platelet activator and inducer of the release of Gas6 (Ishimoto and Nakano, FEBS Lett. 446:197-199 (2000), incorporated herein by reference). Fully activated platelets bind tightly to the fibrin network deposited around them. Histological observations show that both platelets and fibrin are necessary for the formation of a stable coronary thrombus in humans (Falk et al. Interrelationship between atherosclerosis and thrombosis. In Vanstraete et al. (editors), Cardiovascular Thrombosis Thrombocardiology and Thromboneurology. Philadelphia: Lipincott-Raven Publishers (1998), pp. 45-58, incorporated herein by reference). Another platelet adhesion molecule, amphoterin, is translocated to the platelet surface during activation, and binds anionic phospholipid (Rouhainen et al., Thromb. Hemost. 84:1087-1094 (2000), incorporated herein by reference). Like Gas6, amphoterin could form a bridge during platelet aggregation.

The question arises whether it is possible to inhibit these amplification mechanisms but not the initial platelet aggregation step, thereby preventing thrombosis without increasing hemorrhage. The importance of cellular amplification has recently been established by studies of mice with targeted inactivation of Gas6 (Angelillo-Scherrer et al., 2001). The $Gas6^{-/-}$ mice were found to be protected against thrombosis and embolism induced by collagen and epinephrine. However, the $Gas6^{-/-}$ mice did not suffer from spontaneous hemorrhage and had normal bleeding after tail clipping. Furthermore, antibodies against Gas6 inhibited platelet aggregation in vitro as well as thrombosis induced in vivo by collagen and epinephrine. In principle, such antibodies, or ligands competing for Gas6 binding to receptor tyrosine kinases, might be used to inhibit thrombosis. However, in view of the potency of humoral amplification, it might be preferable to inhibit that step. Ideally such an inhibitor would also have additional suppressive activity on the Gas6-mediated cellular amplification mechanism.

A strategy for preventing both cellular and humoral amplification of platelet aggregation is provided by the annexins, a family of highly homologous antithrombotic proteins of which ten are expressed in several human tissues (Benz and Hofmann, Biol. Chem. 378:177-183 (1997), incorporated herein be reference). Annexins share the property of binding calcium and negatively charged phospholipids, both of which are required for blood coagulation. Under physiological conditions, negatively charged phospholipid is mainly supplied by phosphatidylserine (PS) in activated or damaged cell membranes. In intact cells, PS is confined to the inner leaflet of the plasma membrane bilayer and is not accessible on the surface. When platelets are activated, the amounts of PS accessible on their surface, and therefore the extent of annexin binding, are greatly increased (Sun et al., Thrombosis Res. 69:289-296 (1993), incorporated herein by reference). During activation of platelets, microvesicles are released from their surfaces, greatly increasing the surface area expressing anionic phospholipids with procoagulant activity (Merten et al., Circulation 99:2577-2582 (1999); Chow et al., J. Lab. Clin. Med. 135:66-72 (2000), both incorporated herein by reference). These may play an important role in the propagation of platelet-mediated arterial thrombi. Proteins involved in the blood coagulation cascade (factors X, Xa, and Va) bind to membranes bearing PS on their surfaces, and to one another, forming a stable, tightly bound prothrombinase complex. Several annexins, including II, V, and VIII, bind PS with high affinity, thereby preventing the formation of a prothrombinase complex and exerting antithrombotic activity.

4. Medical Devices

Platelets and white blood cells respond to foreign substances in much the same way as an injured tissue (i.e., for example, a blood vessel). Although it is not necessary to understand the mechanism of an invention, it is believed that platelet adherence, followed by fibrin deposition and subsequent encapsulation, is involved in fibrin sheath formation. Fibrin sheaths are known to be responsible for intravascular catheter medical complications, in particular, when using central venous and intraperitoneal dialysis catheters. Santilli, J., "Fibrin Sheaths And Central Venous Catheter Occlusions: Diagnosis And Management" *Tech. in Vascular and Interventional Radiology* 5:89-94 (2002). In one embodiment, the present invention contemplates a method to prolong catheter function comprising coating the outside surface of an intravascular catheter with a drug combination comprising tPA and Annexin A2.

Platelets are also known to release growth factors, in particular, platelet-derived growth factor (PGDF) which promote smooth muscle cell proliferation. Schwartz et al., "Common Mechanisms Of Proliferation Of Smooth Muscle In Atherosclerosis And Hypertension" Hum Pathol. 18:240-247 (1987). For example, following stent placement in patients with coronary lesions, platelets adhere to the injured blood vessel's intraluminal surface. Subsequently, the bound platelets release growth factors that result in restenosis. Restenosis is a condition where smooth muscle cells accumulate within an injured blood vessel such that vessel blockage occurs within 3-6 months (i.e., such as following an intravascular stent placement). Restenosis may be reduced with the use of drug-eluting stents, in particular with drugs such as rapamycin. Falotico et al., "Drug/Drug Delivery Systems For The Prevention And Treatment Of Vascular Disease" United States Patent Application Publ. No: 2002/0016625 A1 Filed: May 7, 2001. Published: Feb. 7, 2002. However, thrombus formation following stent placement is a problem. Jeremias et al., "Stent Thrombosis After Successful Sirolimus-Eluting Stent Implantation" Circulation 109(16):1930-1932 Epub Apr. 12 (2004). Stent technology is attempting to solve this problem using antiplatelet drug-eluting stents or grafts, but its efficacy is as yet unknown. Falotico, R., "Coated Medical Devices For The Prevention And Treatment Of Vascular Disease" United States Patent Application 2003/0216699 A1. Filed: May 7, 2003. Published; Nov. 20, 2003. The present invention contemplates administering a drug combination comprising tPA and Annexin A2 at, or near, an intravascular stent placement.

Platelet-mediated thrombosis is also known to complicate successful native and synthetic graft implantation. Hemodialysis vascular access sites or an obstructed arterial vasculature (i.e., for example, in the vascular periphery or the heart) bypass utilize these grafts. Vascular neointimal formations are known to occur in native and synthetic grafts, particularly in the venous outflow tracts. Walles et al., "Functional Neointima Characterization Of Vascular Prostheses In Human" Ann Thorac Surg. 77:864-868 (2004). Vascular neointimal formations (i.e., for example, lesions) are composed primarily of smooth muscle cells, and ultimately lead to a decreased blood flow within the grafts. Platelet-released growth factors may, in part, stimulate vascular neointimal formations. As a neointimal lesion develops, blood flow becomes more turbulent and further injury occurs, resulting in additional platelet recruitment. With additional platelet recruitment, fibrin deposition may result with complete graft failure as a probable consequence. Thus, a drug combination comprising tPA and Annexin A2 may have distinct advantages over currently recommended antiproliferative and/or anticoagulant therapies. In one embodiment, the present invention contemplates devices and methods to administer a drug combination to a graft venous outflow tract. In one embodiment, a drug combination is administered comprising tPA and Annexin A2. In one embodiment, the medium or carrier may be wrapped or draped around the exterior graft surface such that the drug combination diffuses to an intraluminal blood vessel surface (i.e., for example, the vaso vasorum).

Another embodiment of the present invention contemplates coating a medical device with a medium or carrier comprising tPA and Annexin A2. A medical device is "coated" when a medium comprising tPA and Annexin A2 becomes attached to the surface of the medical device. For example, such attachment includes, but is not limited to, surface adsorption, impregnation into the material of manufacture, covalent or ionic bonding and simple friction adherence to the surface of the medical device.

Carriers or mediums contemplated by this invention may comprise a polymer including, but not limited to, gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

C. Pulmonary Embolisms

A pulmonary embolus is a blockage of an artery in the lungs by fat, air, blood clot, or tumor cells. Pulmonary emboli are most often caused by blood clots in the veins, especially veins in the legs or in the pelvis (hips). More rarely, air bubbles, fat droplets, amniotic fluid, or clumps of parasites or tumor cells may obstruct the pulmonary vessels.

One cause of a pulmonary embolism is a blood clot in the veins of the legs, called a deep vein thrombosis (DVT) (supra). Many clear up on their own, though some may cause severe illness or even death.

Risk factors for a pulmonary embolus may include, but are not limited to: i) Prolonged bed rest or inactivity (including long trips in planes, cars, or trains); ii) Oral contraceptive use; iii) Surgery (especially pelvic surgery); iv) Childbirth; v) Massive trauma; vi) Burns; vii) Cancer; viii) Stroke; ix) Heart attack; x) Heart surgery; or xi) Fractures of the hips or femur. Further, persons with certain clotting disorders and/or autoimmune diseases (i.e., for example, anti-cardiolipin antibody syndrome) may also have a higher risk.

Symptoms of pulmonary embolism may be vague, or they may resemble symptoms associated with other diseases. Symptoms can include, but are not limited to: i) Sudden cough; ii) Bloody sputum (significant amounts of visible blood or lightly blood streaked sputum); iii) Sudden onset of shortness of breath at rest or with exertion; iv) splinting of ribs with breathing (bending over or holding the chest); v) chest pain; vi) rapid breathing; or vii) rapid heart rate (tachycardia)

Pulmonary emboli may be identified using tests including, but not limited to: i) Arterial blood gases; ii) Pulse oximetry; iii) Chest x-ray; iv) Pulmonary ventilation/perfusion scan; v) Pulmonary angiogram; vi) electrocardiogram; and v) computerized tomographic chest angiogram.

D. Superficial Thrombophlebitis

Thrombophlebitis is swelling (inflammation) of a vein caused by a blood clot. Such conditions are usually a result of sitting for a long period of time (such as on a long airplane trip). Disorders that increase a person's chance for blood clots also lead to thrombophlebitis. Superficial thrombophlebitis affects veins near the skin surface.

Symptoms often associated with superficial thrombophlebitis may include but are not limited to: i) Warmth and tenderness over the vein; ii) Pain in the part of the body affected; iii) Skin redness (not always present); or iv) Inflammation (swelling) in the part of the body affected. Objective tests may be performed to detect thrombophlebitis including, but not limited to: i) Doppler ultrasound; ii) Venography; and iii) Blood coagulation studies.

V. Pharmaceutical Formulations

The present invention further provides pharmaceutical compositions (e.g., comprising the Annexin A2/tPA combinations described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual peptide combinations, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the peptide combination is administered in maintenance doses, ranging from 0.01 µg to 100 g per kg of body weight, once or more daily, to once every 20 years.

VI. Drug Delivery Systems

The present invention contemplates several drug delivery systems that provide for the administration of a roughly uniform distribution, having controllable rates of release, of a combination of Annexin A2 and tPA. A variety of different media are described below that are useful in creating such drug delivery systems. It is not intended that any one medium or carrier is limiting to the present invention. Note that any medium or carrier may be combined with another medium or carrier; for example, in one embodiment a polymer microparticle carrier attached to a compound may be combined with a gel medium.

Carriers or mediums contemplated by this invention comprise a material selected from the group comprising gelatin, collagen, cellulose esters, dextran sulfate, pentosan polysulfate, chitin, saccharides, albumin, fibrin sealants, synthetic polyvinyl pyrrolidone, polyethylene oxide, polypropylene oxide, block polymers of polyethylene oxide and polypropylene oxide, polyethylene glycol, acrylates, acrylamides, methacrylates including, but not limited to, 2-hydroxyethyl methacrylate, poly(ortho esters), cyanoacrylates, gelatin-resorcin-aldehyde type bioadhesives, polyacrylic acid and copolymers and block copolymers thereof.

One embodiment of the present invention contemplates a medical device comprising several components including, but not limited to, a reservoir comprising tPA/Annexin A2, a catheter, a sprayer or a tube. In one embodiment, said medical device administers either an internal or external spray to a patient. In another embodiment, said medical device administers either an internal or external gel to a patient.

Microparticles

One embodiment of the present invention contemplates a medium comprising a microparticle. Preferably, microparticles comprise liposomes, nanoparticles, microspheres, nanospheres, microcapsules, and nanocapsules. Preferably, some microparticles contemplated by the present invention comprise poly(lactide-co-glycolide), aliphatic polyesters including, but not limited to, poly-glycolic acid and poly-lactic acid, hyaluronic acid, modified polysaccharides, chitosan, cellulose, dextran, polyurethanes, polyacrylic acids, pseudo-poly(amino acids), polyhydroxybutrate-related copolymers, polyanhydrides, polymethylmethacrylate, poly (ethylene oxide), lecithin and phospholipids.

Liposomes

One embodiment of the present invention contemplates liposomes capable of attaching and releasing tPA and Annexin A2. Liposomes are microscopic spherical lipid bilayers surrounding an aqueous core that are made from amphiphilic molecules such as phospholipids. For example, a liposome may comprise tPA and Annexin A2 trapped between hydrophobic tails of the phospholipid micelle. In addition to these peptides, water soluble drugs can be entrapped in the core and lipid-soluble drugs can be dissolved in the shell-like bilayer. Liposomes have a special characteristic in that they enable water soluble and water insoluble chemicals to be used together in a medium without the use of surfactants or other emulsifiers.

Liposomes form spontaneously by forcefully mixing phospholipids in aqueous media. Water soluble compounds are dissolved in an aqueous solution capable of hydrating phospholipids. Upon formation of the liposomes, therefore, these compounds are trapped within the aqueous liposomal center. The liposome wall, being a phospholipid membrane, holds fat soluble materials such as oils. Liposomes provide controlled release of incorporated compounds. In addition, liposomes can be coated with water soluble polymers, such as polyethylene glycol to increase the pharmacokinetic half-life. One embodiment of the present invention contemplates an ultra high-shear technology to refine liposome production, resulting in stable, unilamellar (single layer) liposomes having specifically designed structural characteristics. These unique properties of liposomes, allow the simultaneous storage of normally immiscible compounds and the capability of their controlled release.

The present invention contemplates cationic and anionic liposomes, as well as liposomes having neutral lipids comprising tPA and Annexin A2. Preferably, cationic liposomes comprise negatively-charged materials by mixing the materials and fatty acid liposomal components and allowing them to charge-associate. Clearly, the choice of a cationic or anionic liposome depends upon the desired pH of the final liposome mixture. Examples of cationic liposomes include lipofectin, lipofectamine, and lipofectace.

One embodiment of the present invention contemplates a medium comprising liposomes that provide controlled release of tPA and Annexin A2. Preferably, liposomes that are capable of controlled release: i) are biodegradable and non-toxic; ii) carry both water and oil soluble compounds; iii) solubilize recalcitrant compounds; iv) prevent compound oxidation; v) promote protein stabilization; vi) control hydration; vii) control compound release by variations in bilayer composition such as, but not limited to, fatty acid chain length, fatty acid lipid composition, relative amounts of saturated and unsaturated fatty acids, and physical configuration; viii) have solvent dependency; iv) have pH-dependency and v) have temperature dependency.

The compositions of liposomes are broadly categorized into two classifications. Conventional liposomes are generally mixtures of stabilized natural lecithin (PC) that may comprise synthetic identical-chain phospholipids that may or may not contain glycolipids. Special liposomes may comprise: i) bipolar fatty acids; ii) the ability to attach antibodies for tissue-targeted therapies; iii) coated with materials such as, but not limited to lipoprotein and carbohydrate; iv) multiple encapsulation and v) emulsion compatibility.

Liposomes may be easily made in the laboratory by methods such as, but not limited to, sonication and vibration. Alternatively, compound-delivery liposomes are commercially available. For example, Collaborative Laboratories, Inc. are known to manufacture custom designed liposomes for specific delivery requirements.

Microspheres, Microparticles and Microcapsules

Microspheres and microcapsules are useful due to their ability to maintain a generally uniform distribution, provide stable controlled compound release and are economical to produce and dispense. Preferably, an associated delivery gel or the compound-impregnated gel is clear or, alternatively, said gel is colored for easy visualization by medical personnel. One of skill in the art should recognize that the terms "microspheres, microcapsules and microparticles" (i.e., measured in terms of micrometers) are synonymous with their respective counterparts "nanospheres, nanocapsules and nanoparticles" (i.e., measured in terms of nanometers). It is also clear that the art uses the terms "micro/nanosphere, micro/nanocapsule and micro/nanoparticle" interchangeably, as will the discussion herein.

Microspheres can be obtainable commercially (Proleasee, Alkerme's: Cambridge, Mass.) wherein tPA and Annexin A2 may be homogenized in a suitable solvent and sprayed to manufacture microspheres in the range of 20 to 90 µm. Techniques are then followed that maintain sustained release integrity during phases of purification, encapsulation and storage. Scott et al., Improving Protein Therapeutics With Sustained Release Formulations, Nature Biotechnology, Volume 16:153-157 (1998).

Modification of the microsphere composition by the use of biodegradable polymers can provide an ability to control the rate of tPA/Annexin A2 release. Miller et al., Degradation Rates of Oral Resorbable Implants {Polylactates and Polyglycolates: Rate Modification and Changes in PLA/PGA Copolymer Ratios, J. Biomed. Mater. Res., Vol. 1:711-719 (1977).

Alternatively, a sustained or controlled release microsphere preparation is prepared using an in-water drying method, where an organic solvent solution of a biodegradable polymer metal salt is first prepared. Subsequently, a dissolved or dispersed medium of tPA/Annexin A2 is added to the biodegradable polymer metal salt solution. The weight ratio of tPA/Annexin A2 to the biodegradable polymer metal salt may for example be about 1:100000 to about 1:1, preferably about 1:20000 to about 1:500 and more preferably about 1:10000 to about 1:500. Next, the organic solvent solution containing the biodegradable polymer metal salt and tPA/Annexin A2 is poured into an aqueous phase to prepare an oil/water emulsion. The solvent in the oil phase is then evaporated off to provide microspheres. Finally, these microspheres are then recovered, washed and lyophilized. Thereafter, the microspheres may be heated under reduced pressure to remove the residual water and organic solvent.

Other methods useful in producing microspheres that are compatible with a biodegradable polymer metal salt and a tPA/Annexin A2 mixture are: i) phase separation during a gradual addition of a coacervating agent; ii) an in-water drying method or phase separation method, where an antiflocculant is added to prevent particle agglomeration and iii) by a spray-drying method.

In one embodiment the present invention contemplates a medium comprising a microsphere or microcapsule capable of delivering a controlled release of a tPA/Annexin A2 composition for a duration of approximately between 1 day and 6 months. Controlled release microcapsules may be produced by using known encapsulation techniques such as centrifugal extrusion, pan coating and air suspension. Microspheres/microcapsules can be engineered to achieve particular release rates. For example, Oliosphere® (Macromed) is a controlled release microsphere system. These particular microsphere's are available in uniform sizes ranging between 5-500 µm and composed of biocompatible and biodegradable polymers. Specific polymer compositions of a microsphere may control the drug release rate such that custom-designed microspheres are possible, including effective management of the burst effect. ProMaxx® (Epic Therapeutics, Inc.) is a protein-matrix drug delivery system. The system is aqueous in nature and is adaptable to standard pharmaceutical drug delivery models. In particular, ProMaxx® are bioerodible protein microspheres that deliver both small and macromolecular drugs, and may be customized regarding both microsphere size and desired drug release characteristics.

In one embodiment, a microsphere or microparticle comprises a pH sensitive encapsulation material that is stable at a pH less than the pH of the internal mesentery. The typical range in the internal mesentery is pH 7.6 to pH 7.2. Consequently, the microcapsules should be maintained at a pH of less than 7. However, if pH variability is expected, the pH sensitive material can be selected based on the different pH criteria needed for the dissolution of the microcapsules. The encapsulated compound, therefore, will be selected for the pH environment in which dissolution is desired and stored in a pH preselected to maintain stability. Examples of pH sensitive material useful as encapsulants are Eudragit® L-100 or S-100 (Rohm GMBH), hydroxypropyl methylcellulose phthalate, hydroxypropyl methylcellulose acetate succinate, polyvinyl acetate phthalate, cellulose acetate phthalate, and cellulose acetate trimellitate. In one embodiment, lipids comprise the inner coating of the microcapsules. In these compositions, these lipids may be, but are not limited to, partial esters of fatty acids and hexitiol anhydrides, and edible fats such as triglycerides. Lew C. W., Controlled-Release pH Sensitive Capsule And Adhesive System And Method. U.S. Pat. No. 5,364,634 (herein incorporated by reference).

In one embodiment, a microparticle contemplated by this invention comprises a gelatin, or other polymeric cation having a similar charge density to gelatin (i.e., poly-L-lysine) and is used as a complex to form a primary microparticle. A primary microparticle is produced as a mixture of the following composition: i) Gelatin (60 bloom, type A from porcine skin), ii) chondroitin 4-sulfate (0.005%-0.1%), iii) glutaraldehyde (25%, grade 1), and iv) 1-ethyl-3-(3-dimethylaminopropyl)-carbodiimide hydrochloride (EDC hydrochloride), and ultra-pure sucrose (Sigma Chemical Co., St. Louis, Mo.). The source of gelatin is not thought to be critical; it can be from bovine, porcine, human, or other animal source. Typically, the polymeric cation is between 19,000-30,000 daltons. Chondroitin sulfate is then added to the complex with sodium sulfate, or ethanol as a coacervation agent.

Following the formation of a microparticle, a tPA/Annexin A2 composition is directly bound to the surface of the microparticle or is indirectly attached using a "bridge" or "spacer". The amino groups of the gelatin lysine groups are easily derivatized to provide sites for direct coupling of a composition. Alternatively, spacers (i.e., linking molecules and derivatizing moieties on targeting ligands) such as avidin-biotin are also useful to indirectly couple targeting ligands to the microparticles. Stability of the microparticle is controlled by the amount of glutaraldehyde-spacer crosslinking induced by the EDC hydrochloride. A controlled release medium is also empirically determined by the final density of glutaraldehyde-spacer crosslinks.

VII. Kits

In another embodiment, the present invention contemplates kits for the practice of the methods of this invention. The kits preferably include one or more containers containing a vascular disorder treatment method of this invention. The kit can include a medium comprising tPA and Annexin A2. The kit can include a container comprising the medium. The medium can optionally be a liquid. The kit can optionally include medical devices including, but not limited to, injection syringes, intravenous drip bags, intravenous catheters, tubing comprising connector (i.e., for example, Leur Lock connectors) capable of attaching a drip bag to a catheter. The kit can optionally include a pharmaceutically acceptable excipient and/or a drug delivery vehicle (e.g., a liposome). The medium may be provided suspended in the excipient and/or delivery vehicle or may be provided as a separate component which can be later combined with the excipient and/or delivery vehicle.

The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the mediums for treatment of vascular disorders. In particular the disorders can include, but are not limited to, stroke, myocardial infarction, deep vein thrombosis, or pulmonary embolism. While the instructional materials typically comprise written or printed materials they are not limited to such. Any material capable of storing such instructions and communicating them to an end user is contemplated by this invention. Such material include, but are not limited to electronic storage material (e.g., magnetic discs, tapes, cartridges, chips), optical material (e.g., CD ROM), and the like. Such material may include addresses to internet sites that provide such instructional materials.

EXPERIMENTAL

Example I

Preparation of Recombinant Human Annexin A2

Histidine-tagged recombinant Annexin A2 (rA2) was produced in *E. coli*. using a known bacterial expression vector containing full-length human Annexin A2 cDNA (20). Briefly, A full-length human Annexin II cDNA (See, FIG. 5B) was inserted into a histidine-tagged bacterial expression vector, pQE (purchased from Qiagen), between the KpnI and SalI sites (pQE-A2). A mutant A2 (mA2) expression vector that lacks 224 amino acids of the C-terminal was created as follows. A stop codon was introduced at 114 amino acids using an oligonucleotide-based mutagenesis kit (Quick Change, Clontech) and two complement oligonucleotides 5'-GCT-TCTGAGCTATA-GGCTTCCATGAAG-3' (SEQ ID NO: 3) and 5'-CTTCATGGAAGCCTATAGCT-CAGAAGC-3' (SEQ ID NO: 4) according to the manufacturer's instructions. The mutated sequence was confirmed by DNA sequencing. A cell lysate prepared from overnight cultures of pQE-AN II-transformed JM109 was pelleted (8000 rpm, 15 minutes), resuspended in a buffer containing 50 mmol/L sodium phosphate and 300 mmol/L NaCl (pH8), and sonicated for 2 minutes. The lysate was purified using a nickel-affinity column (His-Trap, purchased from Amersham Pharmacia). Protein purity of rA2 protein was confirmed by SDS-PAGE followed by Coomassie blue staining, and its identity was verified by Western Blot analysis.

Example II

Plasmin Activity Assay

Individual or combined concentrations of rA2, tPA, uPA (100 units/ml), BSA protein were added directly to wells of 96-well culture plate preloaded with N-terminal lysine plasminogen (2.5 µg/ml) and a fluorogenic plasmin substrate (D-Val-Leu-Lys-AMC (200 nM)) in a final volume of 100 µl PBS. After incubation at 37° C. for 30 min, plasmin generation or activity was read on a fluorescent plate reader at excitation 360 nm and emission 460 nm (20). The plate readings were expressed as relative fluorescent units for each well, and the final result was represented as fold of plasmin activity generated by tPA or uPA alone.

Example III

Animal Models of Focal Embolic Cerebral Ischemia

All experiments were performed following an institutionally approved protocol in accordance with the National Institutes of Health Guide for the Care and Use of Laboratory Animals.

Male Wistar rats (270-300 g) were anesthetized with 1-2% isoflurane under spontaneous respiration in a 30% oxygen/70% nitrous oxide mixture. Rectal temperatures were maintained between 37° C. and 38° C. with a thermostat-controlled heating pad. The right femoral artery was cannulated, and physiologic parameters including rectal temperature, mean arterial blood pressure, pH, $PCO_2$, and $PO_2$ were monitored throughout all experiments. The right femoral vein was cannulated for drug administration.

Focal embolic strokes were induced as previously described (2), except that two blood clots, 20-mm in length, were infused. In the appropriate groups, human recombinant tPA (Activase®, Genentech Inc, San Francisco, Calif., U.S.A.) and/or rA2 protein were administered intravenously. An initial 10% bolus dose was followed by continuous infusion of the remaining drug over a 30 minute period. The relatively high dose of tPA was chosen based on the approximately ten-fold difference in fibrin-specific enzyme activity between human and rodent systems (22). Only animals surviving 24 h after stroke were included in the study. Numbers of dead animals were counted in calculating the overall mortality rate for each group of animals. All drug treatments were performed by an investigator blinded to the surgical groups.

Example IV

Laser-Doppler Flowmetry Analysis

Regional cerebral blood flow (rCBF) was monitored continuously by laser-doppler flowmetry (LDF). In brief an LDF probe was positioned 2 mm posterior and 5 mm lateral to the bregma, thus monitoring the rCBF of the middle cerebral artery (MCA). Initial stable records of pre-ischemic baseline were set as 100% for each rat. Following clot infusion, the MCA was considered to have been successfully occluded if the rCBF dropped to less than 30% of the pre-ischemic baseline. Animals with rCBF levels of more than 40% of pre-ischemic baseline were excluded from the study. In the delayed 4 hr treatment study, rCBF was monitored for 2 h after induction of ischemia, and then reprobed in the same position and continuously monitored for 1 h after treatment.

Example V

Analysis of Infarct Volumes

At 24 hours after induction of ischemia, rats were sacrificed with a lethal dose of sodium pentobarbital and transcardially perfused to remove all intravascular blood. Coronal brain sections (2 mm thick) were stained with 2.3.5-triphenyltetrazolium chloride (TTC, Sigma, St. Louis, Mo., U.S.A.). Infarct volumes were quantified using computer-assisted image analysis (2). To eliminate confounding effects of edema and swelling, the indirect method was used (contralateral volume minus un-infarcted ipsilateral volume).

Example VI

Spectrophotometric Assay of Intracerebral Hemorrhage

The volume of intracerebral hemorrhage was quantified using a previously described spectrophotometric hemoglobin assay (2).

Example VII

Measurement of Plasma D-Dimer Levels

Blood samples were collected, anticoagulated upon addition of one-ninth volume of 3.2% (0.109M) trisodium citrate, and centrifuged at 400 g for 15 min. Plasma samples were stored at −80° C. until assayed. D-dimer was assayed on plasma samples diluted 1:4 in an ELISA kit (American Diagnostica Inc, Stamford, Conn., USA) according to the manufacturer's instructions.

Example VIII

Statistical Analysis

Data were expressed as mean+standard error of the mean (S.E.M). The Chi-square test was used to evaluate differences in mortality. rCBF levels, infarct volumes, hemorrhage volumes and D-dimer levels were assessed with ANOVA analysis followed by Tukey-Kramer tests. Differences with $P<0.05$ were considered statistically significant.

REFERENCES

1. Ding G, Jiang Q, Zhang L, et al. Analysis of combined treatment of embolic stroke in rat with r-tPA and a GPIIb/IIIa inhibitor. J Cereb Blood Flow Metab. January 2005; 25(1):87-97.
2. Asahi M, Asahi K, Wang X, et al. Reduction of tissue plasminogen activator induced hemorrhage and brain injury by free radical spin trapping after embolic focal cerebral ischemia in rats. J Cereb Blood Flow Metab. March 2000; 20(3):452-457.
3. Wang X, Tsuji K, Lee S R, et al. Mechanisms of hemorrhagic transformation after tissue plasminogen activator reperfusion therapy for ischemic stroke. Stroke. November 2004; 35(11 Suppl 1):2726-2730.
4. Armstead W M, Nassar T, Akkawi S, et al. Neutralizing the neurotoxic effects of exogenous and endogenous tPA. Nat. Neurosci. September 2006; 9(9):1150-1155.
5. Lapchak P A, Araujo D M, Pakola S, et al. Microplasmin: a novel thrombolytic that improves behavioral outcome after embolic strokes in rabbits. Stroke. September 2002; 33(9):2279-2284.
6. Lapchak P A, Song D, Wei J, et al. Coadministration of NXY-059 and tenecteplase six hours following embolic strokes in rabbits improves clinical rating scores. Exp Neurol. August 2004; 188(2):279-285.
7. Haley E C, Jr., Levy D E, Brott T G, et al. Urgent therapy for stroke. Part II. Pilot study of tissue plasminogen activator administered 91-180 minutes from onset. Stroke. May 1992; 23(5):641-645.
8. Brott T G, Haley E C, Jr., Levy D E, et al. Urgent therapy for stroke. Part I. Pilot study of tissue plasminogen activator administered within 90 minutes. Stroke. May 1992; 23(5):632-640.
9. Zivin J A. Thrombolytic stroke therapy: past, present, and future. Neurology. Jul. 13, 1999; 53(1):14-19.
10. Benchenane K, Berezowski V, Ali C, et al. Tissue-type plasminogen activator crosses the intact blood-brain barrier by low-density lipoprotein receptor-related protein-mediated transcytosis. Circulation. May 3, 2005; 111(17): 2241-2249.
11. Harada T, Kano T, Katayama Y, et al. Tissue plasminogen activator extravasated through the cerebral vessels: evaluation using a rat thromboembolic stroke model. Thromb Haemost. October 2005; 94(4):791-796.
12. Tsirka S E, Rogove A D, Strickland S, Neuronal cell death and tPA. Nature. Nov. 14, 1996; 384(6605):123-124.
13. Benchenane K, Lopez-Atalaya J P, Fernandez-Monreal M, et al. Equivocal roles of tissue-type plasminogen activator in stroke-induced injury. Trends Neurosci. March 2004; 27(3):155-160.
14. Kaur J, Zhao Z, Klein G M, et al. The neurotoxicity of tissue plasminogen activator?J Cereb Blood Flow Metab. September 2004; 24(9):945-963.
15. Tsirka S E. Clinical implications of the involvement of tPA in neuronal cell death. Mol. Med. May 1997; 75(5): 341-347.
16. Kim J, Hajjar K A. Annexin II: a plasminogen-plasminogen activator co-receptor. Front Biosci. Feb. 1, 2002; 7:d341-348.
17. Hajjar K A, Menell J S. Annexin II: a novel mediator of cell surface plasmin generation. Ann N Y Acad. Sci. Apr. 15, 1997; 811:337-349.
18. Hajjar K A, Acharya S S. Annexin II and regulation of cell surface fibrinolysis. Ann N Y Acad. Sci. May 2000; 902: 265-271.
19. Hajjar K A, Krishnan S. Annexin II: a mediator of the plasmin/plasminogen activator system. Trends Cardiovasc Med. July 1999; 9(5):128-138.
20. Ishii H, Yoshida M, Hiraoka M, et al. Recombinant annexin II modulates impaired fibrinolytic activity in vitro and in rat carotid artery. Circ Res. Dec. 7, 2001; 89(12): 1240-1245.
21. Tanaka Y, Ishii H, Hiraoka M, et al. Efficacy of recombinant annexin 2 for fibrinolytic therapy in a rat embolic stroke model: A magnetic resonance imaging study. Brain Res. Aug. 24, 2007; 1165:135-143.
22. Koringer C, Collen D. Studies on the specific fibrinolytic effect of human extrinsic (tissue-type) plasminogen activator in human blood and in various animal species in vitro. Thromb Haemost. Aug. 28, 1981; 46(2):561-565.
23. Morris D C, Zhang L, Zhang Z G, et al. Extension of the therapeutic window for recombinant tissue plasminogen activator with argatroban in a rat model of embolic stroke. Stroke. November 2001; 32(11):2635-2640.
24. Knecht M F, Heinrich F, Spanuth E. Evaluation of plasma D-dimer in the diagnosis and in the course of fibrinolytic therapy of deep vein thrombosis and pulmonary embolism. Thromb Res. Jul. 15, 1992; 67(2):213-220.
25. Marler J R, Goldstein L B. Medicine. Stroke—tPA and the clinic. Science. Sep. 19, 2003; 301(5640):1677.
26. Grotta J C, Burgin W S, El-Mitwalli A, et al. Intravenous tissue-type plasminogen activator therapy for ischemic stroke: Houston experience 1996 to 2000. Arch Neurol. December 2001; 58(12):2009-2013.
27. Nassar T, Akkawi S, Shina A, et al. In vitro and in vivo effects of tPA and PAI-1 on blood vessel tone. Blood. Feb. 1, 2004; 103(3):897-902.
28. Nicole O, Docagne F, Ali C, et al. The proteolytic activity of tissue-plasminogen activator enhances NMDA receptor-mediated signaling. Nat. Med. January 2001; 7(1):59-64.
29. Wang X, Lee S R, Arai K, et al. Lipoprotein receptor-mediated induction of matrix metalloproteinase by tissue plasminogen activator. Nat. Med. October 2003; 9(10): 1313-1317.
30. Sena E, van der Worp H B, Howells D, et al. How can we improve the pre-clinical development of drugs for stroke? Trends Neurosci. September 2007; 30(9):433-439.
31. Sakharov D V, Rijken D C. Superficial accumulation of plasminogen during plasma clot lysis. Circulation. Oct. 1, 1995; 92(7):1883-1890.
32. Siever D A, Erickson H P. Extracellular annexin II. Int J Biochem Cell Biol. November 1997; 29(11):1219-1223.
33. Aarli A, Skeie Jensen T, Kristoffersen E K, et al. Inhibition of phytohaemagglutinin-induced lymphoproliferation by soluble annexin II in sera from patients with renal cell carcinoma. Apmis. September 1997; 105(9):699-704.
34. Pfefferkorn T, Rosenberg G A. Closure of the blood-brain barrier by matrix metalloproteinase inhibition reduces rtPA-mediated mortality in cerebral ischemia with delayed reperfusion. Stroke. August 2003; 34(8):2025-2030.
35. Lapchak P A, Chapman D F, Zivin J A. Metalloproteinase inhibition reduces thrombolytic (tissue plasminogen activator)-induced hemorrhage after thromboembolic stroke. Stroke. December 2000; 31(12):3034-3040.
36. Zhang L, Zhang Z G, Liu X, et al. Treatment of embolic stroke in rats with bortezomib and recombinant human tissue plasminogen activator. Thromb Haemost. January 2006; 95(1):166-173.
37. Zhang L, Zhang Z G, Zhang R, et al. Adjuvant treatment with a glycoprotein IIb/IIIa receptor inhibitor increases the therapeutic window for low-dose tissue plasminogen activator administration in a rat model of embolic stroke. Circulation. Jun. 10, 2003; 107(22):2837-2843.
38. Lapchak P A, Araujo D M, Song D, et al. Effects of the spin trap agent disodium-[tert-butylimino)methyl]benzene-1,3-disulfonate N-oxide (generic NXY-059) on intracerebral hemorrhage in a rabbit Large clot embolic stroke model: combination studies with tissue plasminogen activator. Stroke. June 2002; 33(6):1665-1670.
39. Cheng T, Petraglia A L, Li Z, et al. Activated protein C inhibits tissue plasminogen activator-induced brain hemorrhage. Nat. Med. November 2006; 12(11):1278-1285.
40. Strbian D, Karjalainen-Lindsberg M L, Kovanen P T, et al. Mast cell stabilization reduces hemorrhage formation and mortality after administration of thrombolytics in experimental ischemic stroke. Circulation. Jul. 24, 2007; 116(4): 411-418.

We claim:

1. A method comprising:
   a) providing:
      i) a patient exhibiting at least one fibrin clot associated with a vascular disorder, and
      ii) a medium comprising Annexin A2 and tissue plasminogen activator (tPA);
   b) administering said medium to said patient under conditions such that lysis of said at least one fibrin clot is increased, wherein said at least one fibrin clot is reduced in size by at least 80% in fifteen minutes.

2. The method of claim 1, wherein said vascular disorder is selected from the group consisting of stroke, myocardial infarction, pulmonary embolism, deep vein thrombosis and intracerebral hematoma.

3. The method of claim 1, wherein said Annexin A2 and said tPA have a dose ratio of 2:1.

4. The method of claim 1, wherein said medium comprises a carrier.

5. The method of claim 4, said Annexin A2 and said tPA are attached to said carrier.

6. The method of claim 4, wherein said carrier is selected from the group consisting of a liposome and a microparticle.

7. The method of claim 1, wherein said medium is a liquid.

8. The method of claim 7, wherein said administering is intravenous.

9. The method of claim 1, wherein said patient is a human.

10. The method of claim 1, wherein said patient is a non-human.

11. The method of claim 1, further comprising wherein said at least one fibrin clot is reduced in size by 100% in thirty minutes.

12. A method comprising:
   a) providing:
      i) a human patient exhibiting at least one fibrin clot associated with a recently incurred stroke,
      ii) a medium comprising Annexin A2 and tissue plasminogen activator (tPA), wherein said Annexin A2 and said tPA have a dose ratio of 2:1; and,
   b) administering said medium to said human patient under conditions such that lysis of said at least one fibrin clot is increased.

13. The method of claim 12, wherein said administering occurred less than three hours after said stroke.

14. The method of claim 12, wherein said administering occurred less than six hours after said stroke.

15. The method of claim 12, wherein said administering occurred less than twelve hours after said stroke.

16. The method of claim 12, wherein said tPA dose is at least two-fold lower than the currently recommended dose.

17. The method of claim 12, wherein said tPA dose is at least three-fold lower than the currently recommended dose.

18. The method of claim 12, wherein tPA dose is at least four-fold lower than the currently recommended dose.

19. The method of claim 12, wherein said at least one fibrin clot is reduced in size by at least 80% in fifteen minutes.

20. The method of claim 12, wherein said at least one fibrin clot is reduced in size by 100% in thirty minutes.

* * * * *

SEQUENCE LISTING

```
<160> NUMBER OF SEQ ID NOS: 4

<210> SEQ ID NO 1
<211> LENGTH: 192
<212> TYPE: PRT
<213> ORGANISM: Homo sapiens

<400> SEQUENCE: 1

Met Glu Gln His Phe Leu Gly Cys Val Lys Arg Ala Trp Asp Ser Ala
1               5                   10                  15
```

```
Glu Val Ala Pro Glu Pro Gln Pro Pro Asn Ser Ser Glu Asp Arg
            20                  25                  30

Gly Pro Trp Pro Leu Pro Leu Tyr Pro Val Leu Gly Glu Tyr Ser Leu
         35                  40                  45

Asp Ser Cys Asp Leu Gly Leu Leu Ser Ser Pro Cys Trp Arg Leu Pro
 50                  55                  60

Gly Val Tyr Trp Gln Asn Gly Leu Ser Pro Val Gln Ser Thr Leu
 65                  70                  75                  80

Glu Pro Ser Thr Ala Lys Pro Thr Glu Phe Ser Trp Pro Gly Thr Gln
                 85                  90                  95

Lys Gln Gln Glu Ala Pro Val Glu Glu Val Gly Gln Ala Glu Glu Pro
            100                 105                 110

Asp Arg Leu Arg Leu Gln Gln Leu Pro Trp Ser Ser Pro Leu His Pro
            115                 120                 125

Trp Asp Arg Gln Gln Asp Thr Glu Val Cys Asp Ser Gly Cys Leu Leu
130                 135                 140

Glu Arg Arg His Pro Pro Ala Leu Gln Pro Trp Arg His Leu Pro Gly
145                 150                 155                 160

Phe Ser Asp Cys Leu Glu Trp Ile Leu Arg Val Gly Phe Ala Ala Phe
                165                 170                 175

Ser Val Leu Trp Ala Cys Cys Ser Arg Ile Cys Gly Ala Lys Gln Pro
            180                 185                 190

<210> SEQ ID NO 2
<211> LENGTH: 1182
<212> TYPE: DNA
<213> ORGANISM: Homo sapiens

<400> SEQUENCE: 2
gacccacgcg tccggttcta tgtactctct aaaatgttat cgttttcatt tgtctactaa      60
ttttcgagca tttgttacta ctgagtttct taatatctga ctggcctccg cccacgggct    120
ctgcagagca taaatactca ggctgatggt agtgcagaga ctctccctcc ttgatcagcg    180
caaacgttgg tctgaggctt gagggatgga gcaacatttt cttggctgtg tgaagcgggc    240
ttgggattcc gcagaggtgg cgccagagcc ccagcctcca cctattgtga gttcagaaga    300
tcgtgggccg tggcctcttc ctttgtatcc agtactagga gagtactcac tggacagctg    360
tgatttggga ctgcttttcca gcccttgctg gcggctgccc ggagtctact ggcaaaacgg    420
actctctcct ggagtccaga gccacttgga accaagtaca gcgaagccca ctgagttcag    480
ttggccgggg acacagaagc agcaagaggc acccgtagaa gaggtggggc aggcagagga    540
acccgacaga ctcaggctcc agcagcttcc ctggagcagt cctctccatc cctgggacag    600
acagcaggac accgaggtct gtgacagcgg gtgccttttg aacgccgcc atcctcctgc    660 cctccagccg tggcgccacc tcccgggttt ctcagactgc ctggagtgga ttcttcgcgt    720
tggttttgcc gcgttctctg tactctgggc gtgctgttca cggatctgtg gagctaagca    780
gccttagata gcagcagaag gcttttttgga ttctcctcct tgaaaagatt ctcagttacc    840
aaacgtctcc acctagaaaa taaaaataca ttaagatgtg ctttcattgc tggttgtcag    900 ttttttaaatt ctctttttcc cttatgtttc tttcttgttt cgcgtcgctt attactttca    960
gtttccttgt attttaaata ttggtatttc attaaatatt tcattcgtat ctgttttcac   1020
tttgagaaat ctattttacg attgtagaat cttagagtt tttggcaaat ttaaaatttg    1080
tttttttcca ttgtatttta aaatcttatt cctactattt ttctaattat tgcttttttaa   1140
```

```
atgtattgtt tgtttacatt taattttaaa aaaaaaaaaa aa                  1182

<210> SEQ ID NO 3
<211> LENGTH: 27
<212> TYPE: DNA
<213> ORGANISM: Artificial sequence
<220> FEATURE:
<223> OTHER INFORMATION: Synthetic

<400> SEQUENCE: 3
gcttctgagc tataggcttc catgaag                                   27

<210> SEQ ID NO 4
<211> LENGTH: 27
<212> TYPE: DNA
<213> ORGANISM: Artificial sequence
<220> FEATURE:
<223> OTHER INFORMATION: Synthetic

<400> SEQUENCE: 4
cttcatggaa gcctatagct cagaagc                                   27
```